United States Patent [19]

Gallant et al.

[11] 4,316,249

[45] Feb. 16, 1982

[54] AUTOMATIC HIGH SPEED HOLTER SCANNING SYSTEM

[75] Inventors: Stuart L. Gallant, Pikesville; Paul R. Caron, Columbia, both of Md.; Stanley M. Dunn, West Lafayette, Ind.; Walter E. Palmer, Baltimore, Md.; Ernest G. Schmitt, Ellicott City, Md.; Michael Taddeo, Columbia, Md.

[73] Assignee: Hittman Corporation, Columbia, Md.

[21] Appl. No.: 92,925

[22] Filed: Nov. 9, 1979

Related U.S. Application Data

[63] Continuation-in-part of Ser. No. 79,988, Sep. 28, 1979.

[51] Int. Cl.[3] .............................................. G06F 15/42
[52] U.S. Cl. .................................... 364/417; 128/702; 128/708; 364/487
[58] Field of Search ............... 364/415, 487, 417, 900; 128/696, 700, 702–704, 708–712

[56] References Cited

U.S. PATENT DOCUMENTS

| Re. 29,921 | 2/1979 | Cherry et al. | 128/711 |
|---|---|---|---|
| 3,267,933 | 8/1966 | Mills et al. | 128/712 |
| 3,672,353 | 6/1972 | Crovella et al. | 128/712 |
| 3,824,990 | 7/1974 | Baule | 128/702 |
| 3,832,994 | 9/1974 | Bicher et al. | 128/702 |
| 3,853,119 | 12/1974 | Peterson et al. | 128/708 |
| 3,874,370 | 4/1975 | Harris et al. | 128/702 |
| 3,880,147 | 4/1975 | Gruenke et al. | 128/702 |
| 3,913,567 | 10/1975 | Streckmann | 128/711 |
| 3,940,692 | 2/1976 | Neilson | 128/702 |
| 4,023,564 | 5/1977 | Valiquette et al. | 128/708 |

Primary Examiner—Errol A. Krass
Attorney, Agent, or Firm—Fleit & Jacobson

[57] ABSTRACT

An automatic high speed Holter scanning system operates in a nonautomatic mode or in an automatic mode to receive electrocardiogram signals which have been prerecorded in dissimilar formats having different known parameters, and to process same in accordance with an operator input. The automatic arrhythmia processor of the present invention detects ectopic cardiac information, stores the detected information in time sequence, and selectively reads out and displays the stored ectopic information in response to operator command. In addition, the automatic arrhythmia processor compares QRS complexes in received ECG signals to a desired normal QRS complex, and continuously updates the R-R interval and area of the normal QRS complex following each comparison of the normal QRS complex with the subsequent QRS complexes. The system of the present invention basically comprises a front panel for operator control, an input interface unit, converter unit, freeze memories with freeze memory control, CRT with CRT control, a chart recorder, an arrhythmia detection and scanning system, a central processing unit, and various front panel lamps and indicators.

14 Claims, 28 Drawing Figures

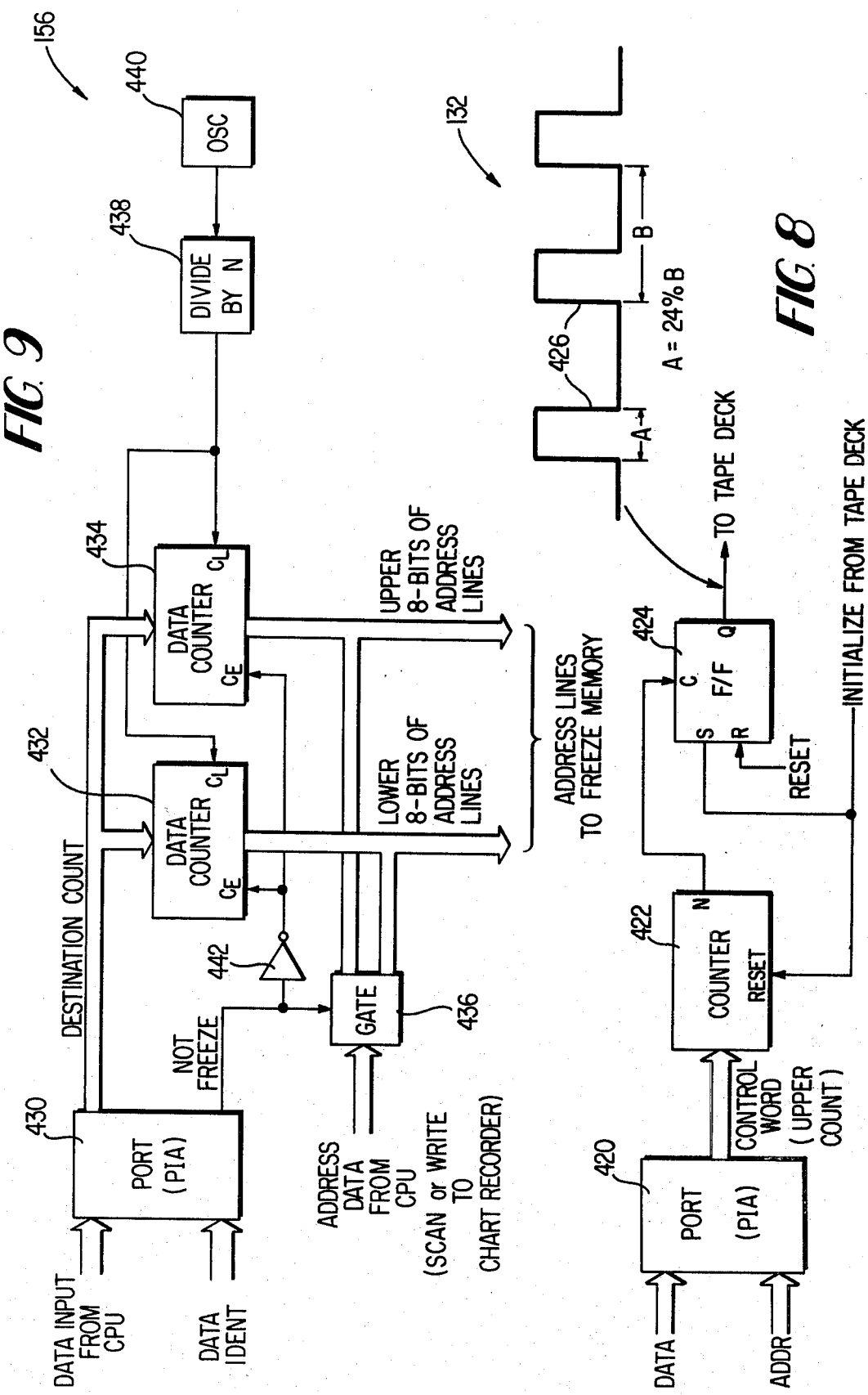

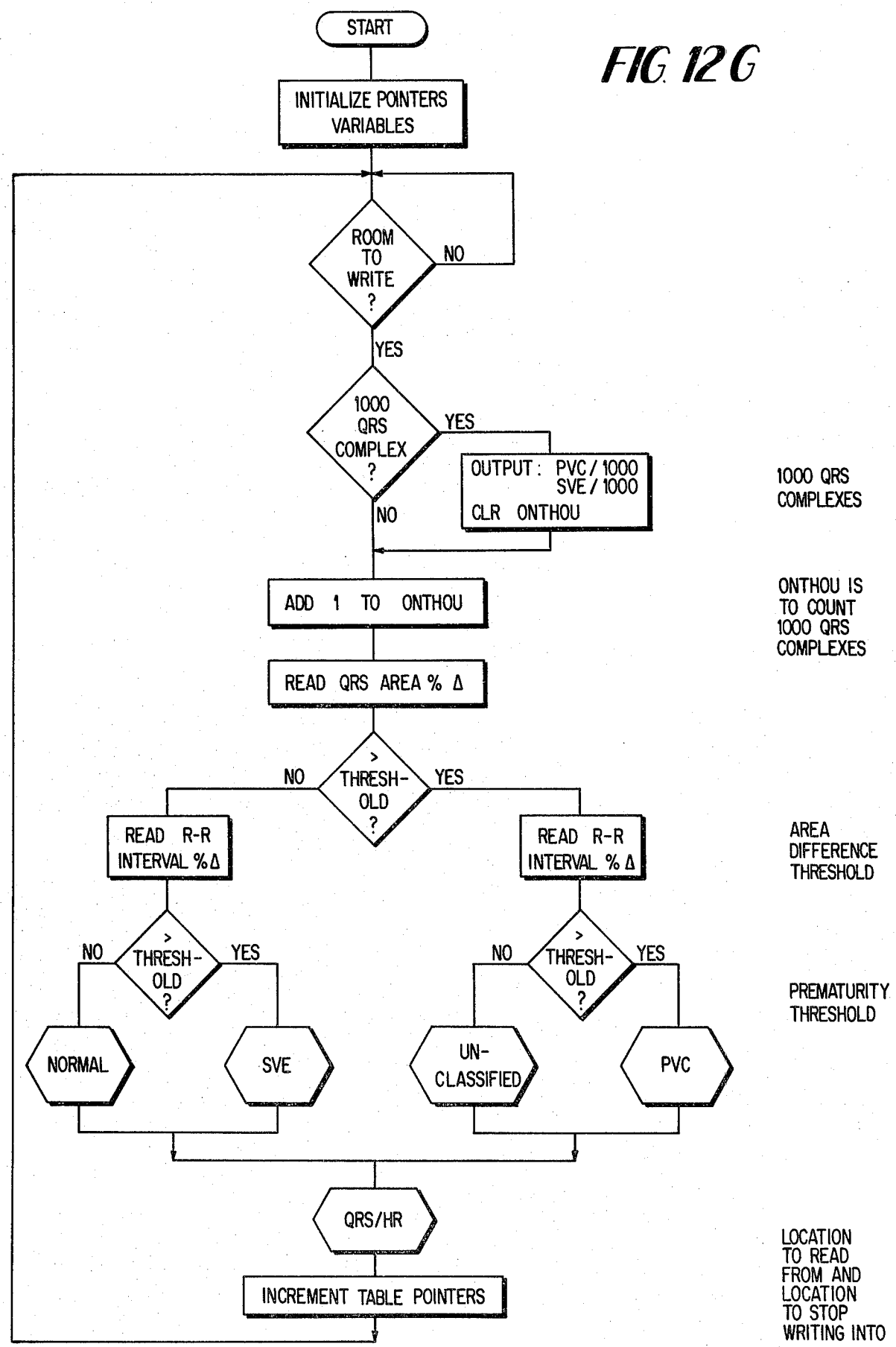

HIERARCHY OF PROGRAMS

AUTOMATIC HIGH SPEED HOLTER SCANNING SYSTEM

This is a continuation-in-part of copending application Ser. No. 79,988, filed on Sept. 28, 1979.

BACKGROUND OF THE INVENTION

The present invention relates to Holter cardiac diagnostic systems and, more specifically, relates to cardiac diagnostic systems which automatically scan Holter tapes to identify ectopic heart beats.

Ever since the inception of the Holter technique in identifying cardiac arrhythmia problems, the manner in which the electrocardiogram results are displayed has been constantly improved. Currently, apparatus is available to display the electrocardiogram signal on an oscilloscope so as to permit a technician to detect visually the ectopic beats. It is also common practice to employ a multichannel strip-chart recorder to provide a permanent record of the desired portions of the Holter tape. Typically, the Holter tape is taken or recorded over a 24-hour period, and it is displayed on an oscilloscope with a skilled technician or operator viewing the tape to identify all ectopic beats. While it does not take 24 hours for a technician to review a complete Holter tape, it is not possible to speed this up to such an extent that a tape may be reviewed in only a few minutes. It typically takes on the order of an hour for a technician to review a single 24-hour Holter tape. Needless to say, this becomes extremely tiring to the technician, resulting in at least an increased probability of errors, which the technician may make during his visual review of the electrocardiogram data.

At the present time, there are commercially available scanners which can operate at speeds up to 120 times real time. Some of these provide limited automatic arrhythmia detection, and generate a summary report. However, prior to the present invention, there has never been a device which can automatically scan at rates up to 240 times real time and produce graphical and alphanumeric summaries of the recorded ectopic activity.

SUMMARY OF THE INVENTION

The present invention provides a Holter cardiac diagnostic system which can operate in a nonautomatic mode, wherein the electrocardiogram tape can be replayed at from 60 to 240 times the real time and in an automatic mode which will identify cardiac arrhythmias at such a high rate that an entire 24-hour electrocardiogram recording may be scanned and analyzed in six minutes. Simultaneously with the automatic scanning, a hard copy report is prepared and a graphic display in color is ready for review and documentation of events of interest which occurred in the course of the 24-hour electrocardiogram. The present invention can accommodate cassette tapes, reel-to-reel tapes or any other type of tape which has been produced by the various Holter recording apparatus now presently available. This is made possible in the present invention by the use of a microprocessor which can be quickly programmed or reprogrammed by the operator by means of a keyboard to accept any of the several different format Holter tape systems now available.

The present invention provides an extremely large real time memory capacity, which is on the order of 512 seconds of electrocardiogram data, i.e., 256 seconds per channel. This large memory capacity permits the operator to scan any cassette tape and, upon selection of a freeze mode of operation, automatically store a total of 512 seconds of the tape, i.e., 256 seconds on each side of the instant in time at which the tape is stopped. In a two-channel situation, this is of course 128 seconds on each side of the specific instant per channel. The advantages provided by the use of such a large real time memory will be set forth hereinbelow. However, this ability to freeze and display an entire 256 seconds worth of electrocardiogram information on an oscilloscope permits the operator to locate very decisively and quickly any abnormalities by viewing large sections of the taped data in a very short time.

During the nonautomatic mode of operation of the present invention, the electrocardiogram tape is replayed at a rate of 60, 120 or 240 times the real time. During this nonautomatic replay operation, each electrocardiogram complex is displayed on the oscilloscope screen via the superimposition method. This method overlays each complex on top of the preceding one. This permits the operator to make a better judgment regarding cardiac arrhythmias. When the operator stops the machine upon discovery of such an apparent arrhythmia, the machine automatically moves to a "freeze" mode, and displays the data in the memory on the screen, as described above. This permits quick recall of the data and a concomitant fast interpretation of cardiac abnormalities, as well as rapid printout of any data which must be recorded in a hard-copy format.

An extremely important feature of the present invention is the automatic scanning capability, which automatically scans and identifies all cardiac arrhythmias occurring in the Holter tape. In this pre-editing or automatic scanning mode, the present invention automatically scans the tape at a rate which is variable and dependent upon the complexity of the data being analyzed. During the scan, the present invention is determining which beats are normal and which beats are abnormal. The abnormal beats are further classified as couplets, runs, or multifocal types of premature ventricular contractions (PVC). It is a further feature of the present invention to permit the operator to adjust the parameters within the automatic arrhythmia processor, which, if exceeded in relation to the updated QRS complex or the complex selected as normal, will indicate an abnormality. This is accomplished by providing to the operator specific controls to adjust the percent prematurity and the percentage area variation from the QRS complex which has been designated normal. Once the Holter tape has been completely scanned in an automatic mode, the data is available to the operator for verification on the oscilloscope screen by two different methods. In a first method, a user may view the data in graphical format which summarizes the 24-hour recorded period and shows heart rate variation, PVC rate variation, supraventricular ectopic beat variation, and other parameters which may be desired. In the second method, the cathode ray tube display is an alphanumeric format listing of the various abnormalities and the time at which they occur. The present invention operates in conjunction with the timing pulses on the Holter tape so as to run in the tape's time frame. Additionally, the present invention provides the capability whereby any abnormal beat occurring within a given minute segment of the tape may be tagged or flagged during the automatic scanning mode. This permits the machine then to find the areas of the tape where abnormal beats occurred and does not require manually rescanning the tape.

In addition to the visual data on the oscilloscope, the data may also be provided in a hard-copy form. The hard-copy form can be produced by a two-channel chart writer which reproduces the traces shown on the oscilloscope screen, or an auxiliary alphanumeric printer may be employed for reproducing the alphanumeric data, which was summarized in a tabular format.

The inventive apparatus can also be utilized to search for a predetermined time of the day which correlates with an entry in the patient's diary. By means of this feature, the scan time is reduced when the operator wishes to immediately observe specific events which were indicated in the patient's diary. Additionally, the Holter tape can be rapidly advanced to any time of day once the time initialization has been placed into the memory of the present invention. This is easily accomplished with Holter tapes produced by the corresponding apparatus designed in accordance with the present invention, but it is also simply initialized with tapes produced on other apparatus. In those cases, the beginning time must be initialized by noting in the patient diary the time the Holter tape recording began and entering this time on the keyboard of the present invention. The time entered will then appear on a digital time display indicating the beginning time of the tape.

The features of the present invention which are considered of great importance are the arrhythmia processing unit, the simultaneous display of dual-channel data on a single-beam CRT, and the capability of the inventive system to accept tapes recorded in any Holter format.

With respect to the first of these features, the inventive system is capable of automatically scanning a Holter tape, recognizing ectopic beats at extremely high speeds, and displaying (in hard-copy or otherwise) information such as the types of ectopic beats, the locations of ectopic beats, and the number of ectopic beats per unit time.

The second feature is made possible by unique electronic processing wherein two channels of simultaneous ECG information are displayed, one above the other, on the screen of a single beam CRT. With the inventive system, the two channels of ECG information are in alignment; that is, a first channel of an ECG event displayed on the top of the screen is in time-alignment with a second channel representing the same ECG event.

The third feature is accomplished by preprogramming into the inventive system, specific parameters of various "Holter" manufacturers, parameters such as the type of modulation used, the recording speed, etc. Then, by entering a code into the system, representative of a specific manufacturer's format, the system can internally set parameters which will enable accurate playback of that particular manufacturer's tape.

Therefore, it is an object of the present invention to provide a Holter cardiac diagnostic system which operates at extremely high speeds relative to the length of time taken to produce the cardiac tape.

It is another object of the present invention to provide a cardiac diagnostic system which employs large real time memory capacity.

It is a further object of the present invention to provide a Holter cardiac diagnostic system which can automatically identify cardiac arrhythmias in a Holter tape.

It is still a further object of the present invention to provide a cardiac diagnostic system which can automatically scan and identify cardiac arrhythmias contained within a 24-hour Holter tape in approximately six minutes.

It is still a further object of the present invention to provide a cardiac diagnostic system which can accept and operate on Holter tapes produced by, and commercially available from, a "Holter" manufacturer.

It is another object of the present invention to provide a cardiac diagnostic system which produces a hard-copy, in alphanumeric format, of the data being analyzed, as well as a strip chart showing the pulse beats.

It is another object of the present invention to provide a cardiac diagnostic system having a two-scan visual output, one being an oscilloscope output showing the actual electrocardiogram traces, and the other being a graphic display cathode ray tube which shows a summary of the Holter tape analysis.

It is still a further object of the present invention to provide a cardiac diagnostic system which automatically scans a Holter tape to identify cardiac arrhythmias wherein the criteria for defining a cardiac arrhythmia and the patient's normal electrocardiogram may be controlled by the operator.

The manner in which these and other objects of the present invention are achieved will become clear from the following detailed description of a preferred embodiment.

BRIEF DESCRIPTION OF THE DRAWINGS

FIG. 8 is a block diagram of the speed control unit portion of the input interface 132 of FIG. 3;

FIG. 9 is a block diagram of the freeze memory controller 156 of FIG. 3;

FIGS. 12A–12J are flowcharts of the operation of the microprocessor unit (MPU) 212 of FIG. 4.

DETAILED DESCRIPTION OF THE PREFERRED EMBODIMENT

Figure 1:
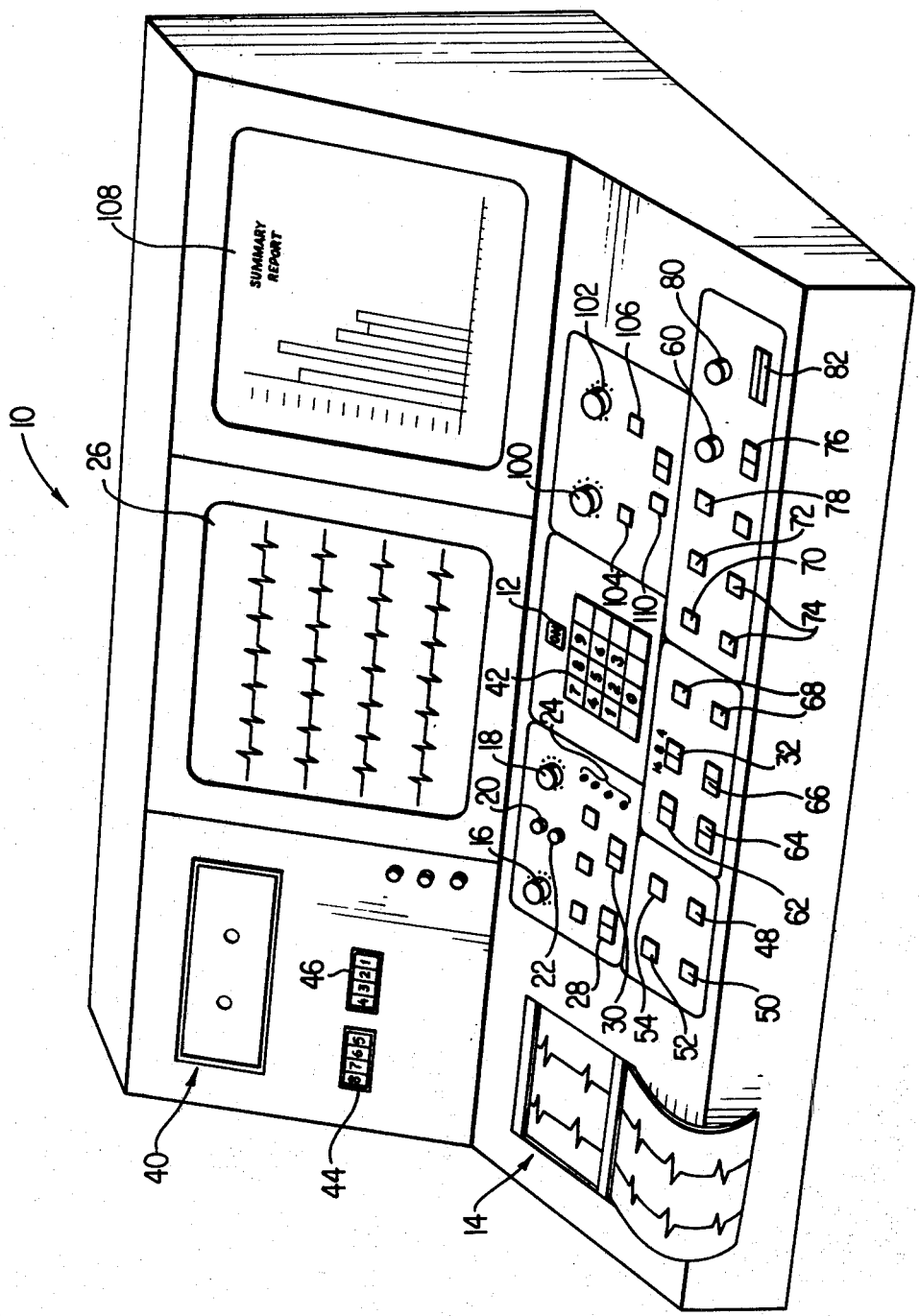
FIG. 1 is a perspective of a control panel and display console of the present invention.

FIG. 1 is a perspective of the apparatus embodying the present invention and shows all of the input and output devices, as well as the controls, except for the alphanumeric hard-copy printer, which may be located adjacent this console or formed integrally therewith. The alphanumeric hard-copy printer may be a commercially available type, such as one manufactured by the Teletype Corporation. By means of FIG. 1, all of the essential operating characteristics of the present invention may be explained. The manner in which these functional characteristics are accomplished will be explained hereinbelow with reference to block diagrams and, where appropriate, detailed circuit diagrams. In FIG. 1, the inventive cardiac diagnostic apparatus 10 is first connected to a suitable source of electrical power and a power switch 12 turned on. A chart recorder, shown typically at 14, is similar to the well-known commercially available chart recorders, and the operator is provided with a control 16, which may be two knobs mounted concentrically for controlling the gain of channel A or channel B, respectively, on the chart recorder. Similarly, two knobs are mounted concentrically at 18 and serve to control the pen position for the two channels. Also provided are controls 20 and 22, which control the heat of the pen and serve to control the darkness or density of the trace being formed on the strip chart. These switches are standard switches found with most conventional, commercially available strip-chart recorders. However, four additional controls, shown generally at 24, are provided and these four switches or buttons indicate the line, on the cathode ray tube oscilloscope monitor 26, that the operator desires to have printed on the strip-chart recorder. One or more of these buttons, including all four, may be depressed at any one time and the appropriate information on the oscilloscope display 26 will then appear and be written out on the chart recorder. The amount of data, i.e., the data corresponding to a number of seconds on the electrocardiogram tape, that will be written to the chart paper is determined by a "zoom" control, which will be explained in detail hereinbelow. A printing-speed switch 28 is provided to control the speed at which the chart recorder will operate, and has the capability of causing the chart recorder to operate at 25 mm per second or at 50 mm per second. Also provided is an automatic index switch 30 which will cause the chart recorder to automatically advance to the beginning of the next full page of paper after printing a requested segment of electrocardiogram data from the monitor 26.

The chart recorder format is such that when activated by depessing the appropriate line number button 24, the chart recorder 14 will automatically write to the chart paper the requested line numbers from memory at the selected chart speed. The number of seconds of data contained in each line is determined by the zoom control 32 as follows. The zoom control may cause the chart recorder to record 16 seconds per line, 8 seconds per line or 4 seconds per line.

A tape deck 40 is used to input the Holter-type cardiac diagnostic tapes and is mounted having the tape transport exposed so that a cassette containing the Holter tape may be easily inserted. Provision may be made to connect reel-to-reel tape by means of patch cards in the conventional manner.

Because the present invention is intended to accommodate a variety of different manufacturer's Holter tapes, provision is made for the operator to instruct the system as to what type of tape is to be scanned. This is accomplished by entering a tape-type code on a keyboard 42. The various different types of Holter tapes are assigned numbers and the appropriate number is punched on the keyboard 42. The time of day will also be digitally displayed on a time display 44 and, when utilizing tapess made with the companion system to the present invention, the actual time is digitally encoded onto the tape and there is no requirement to initialize the time into the system. However, when scanning Holter tapes produced by equipment of other manufacturers, the beginning time must be initialized. This is accomplished by determining from the patient diary the time that the recording began and entering this time on the keyboard 42. Additionally, the present invention displays the heart rate in a digital manner on a display 46. The tape deck is also provided with a fast reverse button 48 and a fast forward button 50 which allow the tape to be automatically and quickly advanced in the desired direction.

A stop button 52 is provided which button when depressed during the fast forward or fast reverse mode, will cause the unit to go into the scan mode, loading data for a time sufficient to fill the freeze memory. The tape is then automatically stopped and the unit is put into the freeze mode. This button 52 also operates during the search mode and a search button 54 is provided to permit the operator to move the tape to any preselected time. This is accomplished by entering the time desired on the keyboard 42 and the selected time will then be displayed on the digital time display 44. Upon depressing the search button 54, the present invention will automatically move the tape to the selected time and will employ the fast forward or fast reverse as required. The minute which has been specifically selected will then be displayed on the monitor 26.

As indicated above, the present invention employs a memory capable of containing 256 seconds of electrocardiogram memory, i.e., 128 seconds per channel, and at any time the operator switches from a "scan" to a "freeze" or when an automatic "search" time is reached or if an event "stop" switch is enabled, a total of 256 seconds is automatically placed in the memory of the present invention. This 256 seconds, i.e., 128 second per channel, represents 128 seconds (64 seconds per channel) on each side of the time the tape was stopped. In other words, stopping a tape creates a 128-second frame, with the time selected being located at the midpoint of this frame. The present invention provides a capability such that all 256 seconds may be reviewed on the oscilloscope monitor 26 and any segment or segments may be selected therefrom and written to the chart recorder 14. The present invention has the further capability of adding additional memory sections and, for example, an additional 256 seconds of memory might be added so that the apparatus contains 512 seconds of memory. All other functions would then remain the same with this further memory capability being provided.

Several controls are provided to permit the operator to utilize the oscilloscope display 26 to its fullest. One of such controls is a brightness control 60 which permits the operator to vary the brightness of the electrocardiogram trace being displayed on the monitor screen 26. As indicated above, the zoom control 32 controls the number of seconds of the electrocardiogram trace which are displayed on the monitor 26. A roll switch 62 permits the operator to move the electrocardiogram trace retained in the memory across the oscilloscope screen 26 in a forward or reverse direction starting from any moment and continuing for the entire 128 seconds per channel in the memory. A jog switch 64 is also provided to permit the operator to move the electrocardiogram in the memory onto the monitor a line at a time. A freeze select switch 66 is also provided to permit the operator to choose what will actually be displayed on the monitor in the freeze mode. Four lines of electrocardiogram data will always be displayed, and, in a channel A setting, all four lines will be derived from channel A while, in a channel B setting, all four lines will be derived from channel B. An additional center setting is provided wherein lines 1 and 3 of the oscilloscope 26 will be derived from channel A and lines 2 and 4 will be derived from channel B. Once again, the number of seconds per line will be determined by the zoom control 32. Capability is also provided for inverting channel A or channel B in case the electrocardiogram leads have been inadvertently reversed during the patient hook-up. These inverting switches are located at 68.

Additional controls for the oscilloscope display 26 are the automatic arrhythmia scan control 68, which will be explained in detail hereinbelow, and an event enable switch 72 which, when depressed, will cause the present invention to automatically stop and go to the freeze mode whenever the patient activated event marker has occurred on the tape during a scan. The operator is in control of the speed at which the tape will be replayed and the three switches 74 are provided to permit the operator to control this tape speed. The tape speeds available are 60, 120 and 240, and depression of the appropriate switch will cause the invention to replay the electrocardiogram tape at 60 or 120 or 240 times the real time when in the scanning mode. It should be noted that these switches are disabled during the automatic arrhythmia scanning mode and the speed of replay is then controlled by a speed control unit located in an input interface of the inventive device. A channel select switch 76 is provided to permit the operator to select channel A or B, or both, which is to be displayed during the scanning mode. Additionally, a switch is provided to permit the operator to choose the presentation format on the monitor 26 during the scan operation. In a multiple position, superimposed multiple complexes will be displayed on the monitor, while, in the single position, single superimposed complexes will be displayed on the monitor.

Because the present invention provides an audible tone in addition to the visual presentation on the oscilloscope screen 26, a control 80 is provided to permit the operator to adjust the volume of the electrocardiogram audio circuit. As will be explained in more detail below, this circuit is designed to produce an audio tone based on the frequency characteristics of the electrocardiogram and the heart rate. As the tape is scanned, the tone will remain relatively constant during normal sinus rhythm, varying slowly with changes in heart rate. When a different shaped complex or a sudden change in heart rate occurs, the tone being produced will alter quickly and alert the operator to the change. Control 80 serves as a volume control for this audio circuit.

A control is provided to permit the operator to control the scan and freeze modes of the present invention and this control 82 will cause the selected scan operation to begin and, upon depressing the switch to the freeze mode, the 256 seconds of electrocardiogram data will be available for display on the screen. By means of the scan and freeze switch 82 and the zoom switch 32, the operator can determine the electrocardiogram data which will be shown on the monitor 26.

The present invention employs an automatic arrhythmia detection system which utilizes a microprocessor which forms and maintains a template of the patient's normal QRS complex. However, this is even further improved upon since the determination of the normal beats utilized to produce the initial template remains with the operator, i.e., control is always in the hands of the person operating the machine. All that is required is that the operator instruct the system of the present invention to accept 16 seconds of data as normal, and the present invention proceeds automatically with the arrhythmia detection. The present invention can construct the template and, in a manner quite similar to that of the human eye, the present invention will compare each incoming QRS complex against the template to determine if the new complex "looks" the same. Assuming that the incoming beat is sufficiently similar, then the present invention will utilize the incoming beats to update the template originally selected so that the template is always representative of the patient's normal beat, even in the face of substantial changes in the activity and resultant heart rate of the patient. In the case where the incoming beats "look" different from the template, then the invention will calculate the criteria and place the beat in the appropriate abnormal category and exclude it from the template. Additionally, the automatic arrhythmia detection system is in control of the tape replay speed such that, as the data is being analyzed, if the system finds that it cannot analyze the data at the maximum rate, the tape speed will be decreased temporarily. The present invention can complete an automatic scan of a 24-hour Holter tape in as little as 6 minutes.

Figure 2:
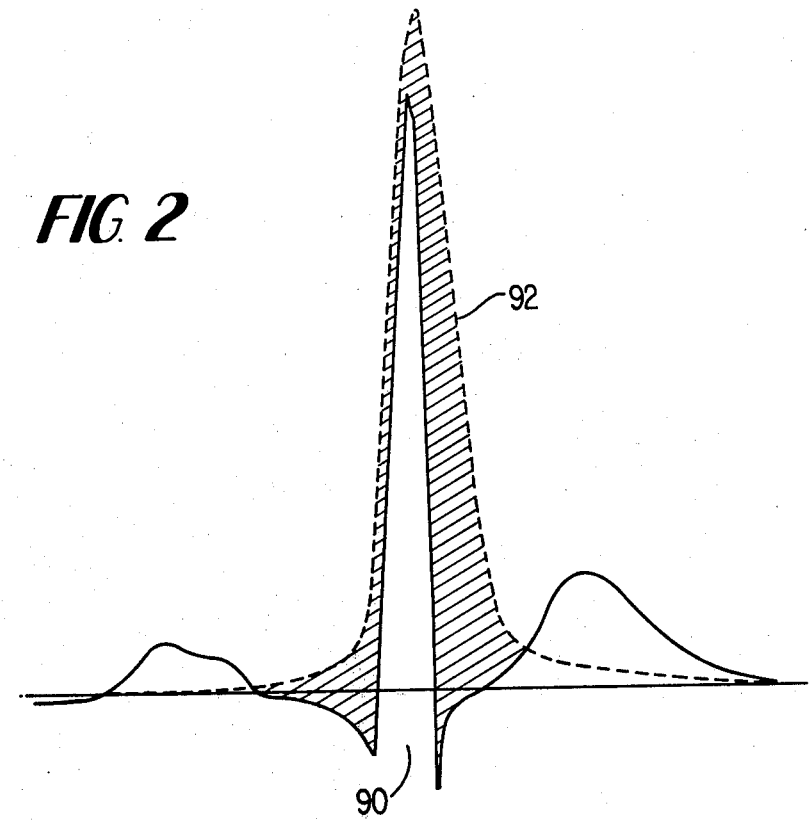
FIG. 2 is a graphical representation of a typical QRS electrocardiogram complex.

As indicated above, the present invention utilizes 16 seconds of electrocardiogram data selected by the operator as being normal in order to form a digital average of the patient's normal heart beat. Each of the operator selected beats is sampled at a real time rate of 256 times per second and the values arranged in an appropriate memory. It is these values that are then utilized by the processor to form the template of the normal beat. Referring to FIG. 2, a typical QRS complex is shown with the reference waveform shown at 90. During the automatic scan mode, the present invention determines if each incoming beat falls within the criteria of the normal heart rate as determined by the R-R interval, and within the selected QRS area difference, as compared to the normal template 90. If the incoming beat meets these criteria, it is then utilized to update the template. In this manner, the template continually changes throughout the 24-hour scan so as to maintain a normal template that is fully representative of the patient's normal complex, even during widely variant activities. The most recent incoming pulse is shown in FIG. 2 at 92.

Referring back to FIG. 1, if the operator first inserts the appropriate tape into the tape deck 40 and, in the event that the tape was not derived from the companion Holter apparatus, the appropriate code is inserted on the keyboard 42 and the system has now been apprised of the type of data which is contained on the Holter tape. The operator then selects the desired percentage of prematurity as indicated in a premature ventricular contraction by means of switch dial 100. With regard to this prematurity, when the initial 16 seconds of normal electrocardiogram trace are selected by the operator, the present invention calculates the R-R average interval and establishes the beginning heart rate for the patient. As each new beat is analyzed, the R-R interval is measured and compared to the previous average R-R interval. The operator can select, by means of the control 100, the percentage of prematurity which will be accepted as normal so as to be anywhere from between 30% and 100% of the average. The present invention is initially designed to automatically accept, as normal, a beat up to 20% late. Accordingly, if the operator selects 80% as the parameter on control 100, then the system will accept all beats which fall within an R-R interval of 80% to 120% of the average. In the event that the beat also meets the area difference criteria, it will then be accepted as normal and will be used to update the template and the average R-R interval. By making the present system dependent on the percentage of the normal R-R interval, the inventive system becomes adaptive and will continuously change as the R-R interval continually changes as the patient goes through his daily activities.

However, the R-R interval is only one criteria and the system also looks at the area difference criteria. This criteria is also controlled by the operator by means of control 102. Once the present invention establishes a normal template 90 (FIG. 2) from the 16 seconds of operator's selected normal electrocardiogram data, the present invention compares each incoming beat against the template to calculate the difference in the area of the new beat and the template. This area difference is shown as the shaded area in FIG. 2. Control 102 permits adjustment of the upper end of the normal area to be adjusted from 40% to 200% difference. For example, setting the area adjustment at 40%, the invention will accept as normal any beat which passes the prematurity criteria and has an area difference of less than 40% from the template. This beat would also then be utilized to update the template and the R-R averages.

Prior to initiating the automatic scan mode, the operator selects the normal ECG data which is to be used to define the initial template. This data is positioned on the first line of the CRT display. When switch 70 is depressed, this data is automatically transferred to the arrhythmia processing section and retained there.

The automatic arrhythmia analyzer also has a control 104 for displaying the analysis in an alphanumeric format and a control 106 for displaying the results graphically on a color graphic display 108. Also provided is a control to print the alphanumeric information. A switch is provided which permits a complete summary report of the procedure, in an hour-by-hour context, or in a minute-by-minute context to be available on the line printer.

Figure 3:
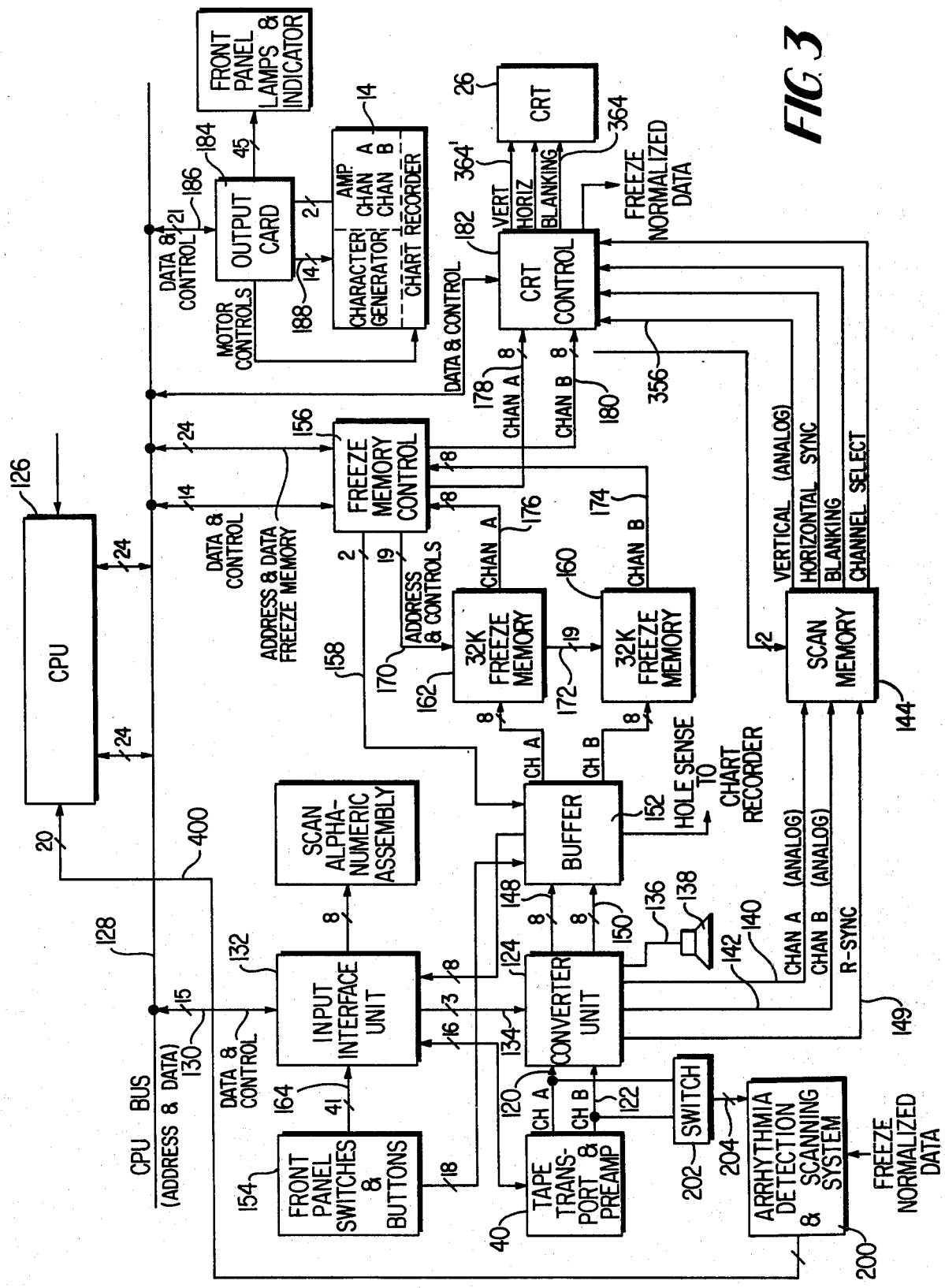
FIG. 3 is a block diagram of the present invention.

Referring now to FIG. 3, the present invention is shown in block diagram form. The data is input from the tape transport unit 40 of FIG. 1 which unit 40 can also contains suitable preamplifier devices to provide the necessary signal gain for processing. Output from the tape transport and preamp unit 40 comprises the data appearing on channel A on multiline 120 and the data appearing on channel B on multiline 122. This data is then provided to a converter unit 124. The converter 124 contains amplifier, filter, and conditioning circuits which process the tape signal. The converter contains a further subsystem which changes the analog signal to a digital signal. This converting subsystem can be a conventional A/D converter. This converter unit 124 may operate at various sample rates. The sample rates are controlled by signals from the central processing unit 126 and the information is provided to the system bus 128, then to an interface unit 132 via lines 130, and then on the three lines 134' to the multiple converter unit 124. The analog signal is also provided on lines 136 to a speaker 138 which, as indicated above, provides the operator with an audible indication of the uniformity of the electrocardiogram signal. When the arrhythmia abnormality appears, a click or pop will be heard from the speaker due to the rapid shift in the analog signal.

The analog signal from channel A and channel B is also provided on lines 140 and 142 to a scan memory unit 144, which will be shown in more detail hereinbelow.

Another function of the converter circuit 124 is to produce an R sync pulse on line 149. This converter circuit 124 then contains a differentiating circuit which serves to determine the location of the R sync pulse in the electrocardiogram signal. It should be noted that the R pulse is not detected by means of the peak detector, but rather by a rate of change of differentiating circuit. Output from the converter unit 124 on lines 148 and 150 comprises the digital data, as converted from the original signal from the tape. This digital data on lines 148 and 150 which correspond, respectively, to channel A and channel B, is fed to a buffer 152. It should be noted that the digital data provided to the buffer 152 is used only for the freeze mode since it is being simply provided to the freeze memory for retention therein. The buffer 152 comprises two tri-state buffers. These buffers are considered to be in the circuit during the freeze mode, as controlled by the front panel switches and buttons 154, and are considered to be out of the circuit during the scanning mode. The control of these two tri-state buffers is from a freeze memory controller unit 156 via control signals provided on line 158 to the buffer circuit 152. This digital data is then provided to four 32K freeze memory units 160 and 162. These memory units comprise conventional static random access memory units which are configured as 32,000 bytes with 8 bits per byte. Because the memories are intended to hold more than 4 minutes worth of information, they are constantly being updated or caused to overflow with old information. In other words, in the absence of a freeze control, the memories merely permit the data to flow through. Upon the operator seeing an apparent arrhythmia, the operator will actuate a freeze control on the front panel, as explained above, and the signal provided on the multiline cable 164 to the input interface unit 132 then proceeds up multiline 130 to the system bus 128 and to the freeze memory controller on line 166 where it ultimately provides a control signal 170 to address the freeze memory units 160 and 162. It should be noted that the two memory units are connected together via a 19-line connection 172. Accordingly, once the freeze control is actuated, the memory will stop at that point and retain all of the information therein and the data will be displayed on the CRT. If the CRT display has been selected, the data will be provided by the freeze memory controller 156 on lines 178 and 180 to a cathode ray tube (CRT) controller unit 182 which will be shown in more detail hereinbelow. Nevertheless, the signals ultimately are displayed on the cathode ray tube display 26. In the event that the information in the memory units 160 and 162 is also desired to be displayed on the strip chart recorder 14, the information is provided by the freeze memory controller 156 on multiline 183 to the system bus and back to an output unit 184 via multilines 186. The information may then be provided on multilines 188 to the strip chart recorder 14.

As indicated above, the present invention provides not only for operator control, but also for an automatic arrhythmia detection and this process is accomplished by means of the automatic arrhythmia detection and scanning system or processor 200. Information is provided to the processor 200 from channel A or channel B via a switch unit 202 which selects one of the channels and feeds it to the processor 200 on lines 204.

Figure 4:
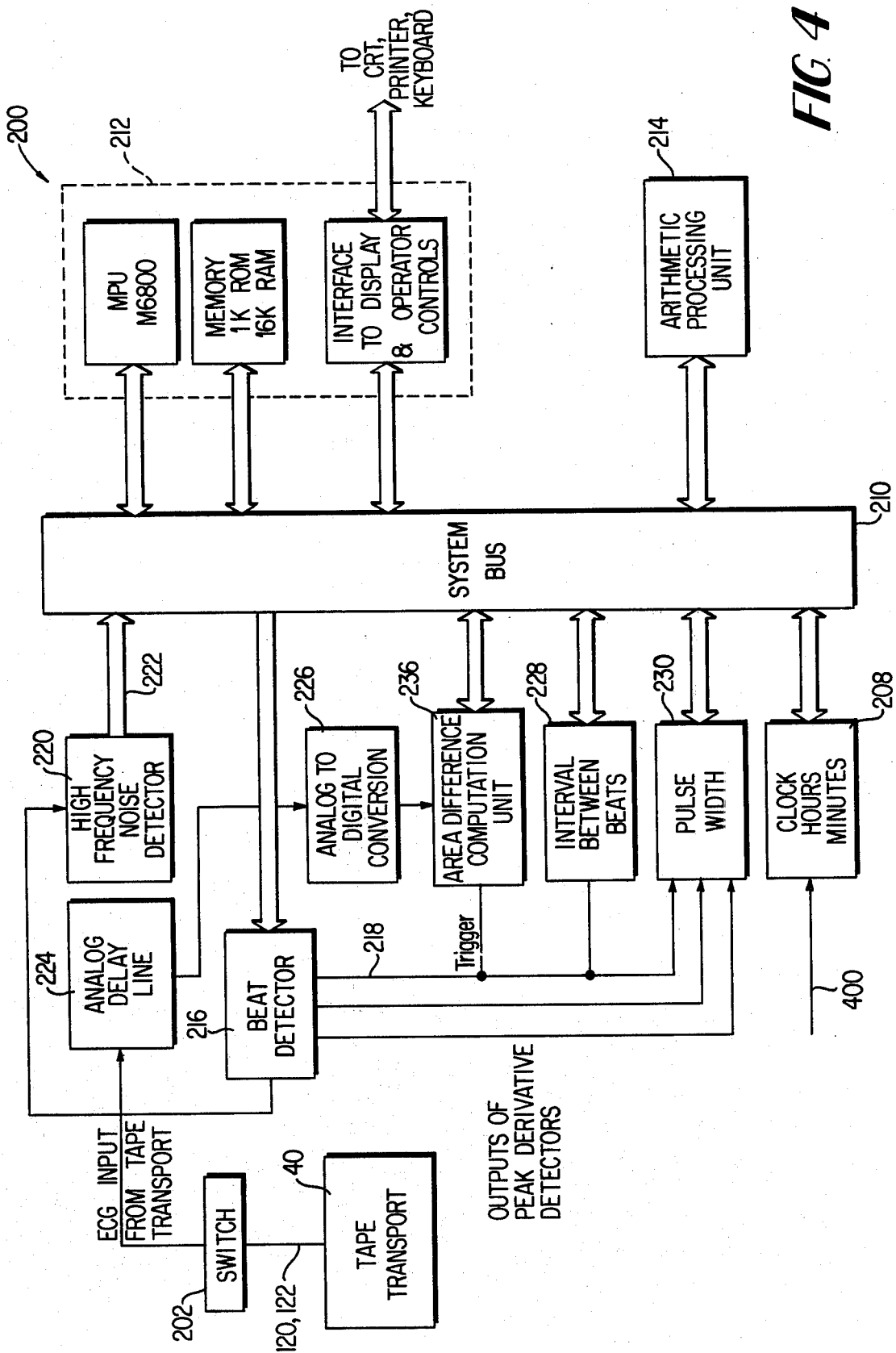
FIG. 4 is a block diagram of the arrhythmia detection and scanning system 200 of FIG. 3.

FIG. 4 is a block diagram of the arrhythmia detection and scanning system 200 described above. The inputs to the detection and scanning system 200 are obtained from the cassette tape transport 40 which plays back the electrocardiogram signal at a rate which is greater than the rate at which the signal is recorded. Additional time data is available to the arrhythmia processor via multibus 400 on lines 120 and 122 from the tape.

The units on the left side of the arrhythmia processor system bus 210 are those elements which are used to extract the specific feature information from the electrocardiogram signal contained on the tape. On the right side of the arrhythmia processor system bus 210 are a microprocessor 212 and an arithmetic processing unit 214. This arithmetic unit 214 is provided to improve the computational speed of the microprocessor system. This subsystem is capable of performing both fixed and floating point arithmetic, as well as basic add, subtract, multiply and divide functions, derived functions, such as trigonometric and exponential functions, plus control and conversion commands. This unit is capable of performing 32-bit floating-point multiplication in approximately 80 microseconds and, accordingly, the arithmetic processing can then proceed in parallel with the microprocessor instruction execution. Typical of the units now available which might be used as the arithmetic processing unit is the Advanced Micro Devices AM 9511 arithmetic processing unit. This arithmetic processing unit 214 serves to compute averages and percentages of the electrocardiogram features in the arrhythmia detection system.

The beat detector 216 produces a trigger signal on line 218 each time the QRS complex occurs in the electrocardiogram signal. Each QRS complex will appear as a predominant sharp spike in the electrocardiogram waveform. The beat detector senses the occurrence of R-waves by detecting positive and negative peaks in the derivative of the electrocardiogram signal. Use of the derivative permits the edges of the R-wave to be accurately located. The analog delay line 224 described below permits the QRS complex to be centered over the stored reference template as shown in FIG. 2. The beat detector 216 includes programmable refractory periods, which inhibit the production of additional trigger pulses for a specified time after a first trigger signal is produced and ensures that only one trigger pulse is produced for each QRS complex. The trigger signal from the beat detector 216 will not occur until after a QRS complex has started; therefore, an analog delay line 224 is provided to delay the electrocardiogram signal which will be used for the area difference computation so that the entire QRS complex can be analyzed in this computation. Conventional analog delay lines may be employed. The high frequency noise detector 220 serves to detect the presence of high frequency noise, i.e., greater than 30 Hz. noise, in the electrocardiogram by monitoring the strength of the frequency components in the electrocardiogram signal above 30 Hz. The signal is then high-press filtered with an active filter and the average magnitude of the high-pass filter output signal is obtained using a full wave rectifier. The average magnitude signal is then compared to a threshold signal with an analog voltage comparator to produce a digital output which is then made available to the microprocessor 212 via line 222 and the system bus 210.

Analog-to-digital conversion of this signal from delay line 224 is performed in order to produce a discrete time digital representation of the electrocardiogram signal which is required for the area difference computation. This analog-to-digital conversion occurs in an 8-bit analog-to-digital converter unit 226 which includes a sample and hold circuit (not shown).

The time interval between successive beats may be measured by a time interval unit 228 which is connected to receive the trigger signal 218 from the beat detector 216. This is accomplished by counting reference clock pulses during the interval between successive trigger pulses from the beat detector 216 in the conventional manner. The beat interval is buffered with a 16-bit latch so that the microprocessor 212 can read the past beat interval while the new one is being measured. The pulse width of the predominant pulse in the electrocardiogram signal is measured by counting reference clock pulses between the leading and the trailing edges of the pulse and this is accomplished in a pulse width determining unit 230. The leading and trailing edges are identified by using the outputs of positive and negative peak derivative detectors in the beat detector 216. The count obtained from each beat must be read by the microprocessor 212 before the next beat occurs. The clock signal from multibus 400, which (via clock storage unit 208) provides the time of day as the electrocardiogram tape is played back, is necessary in order to permit the time of day to be recorded when an arrhythmia occurs.

The area difference computation unit 236 is employed to detect sudden changes in the shape of the QRS complex by comparing each incoming QRS complex to a storage reference QRS complex, previously termed the template. This unit computes an area difference between the reference QRS complex and the QRS complex currently being examined, as shown in FIG. 2. The stored reference QRS complex can be updated as the electrocardiogram tape is analyzed in order to permit the system to track slow changes which may occur in the QRS complexes. The total area of the reference QRS complex is also computed along with the area difference so that it is possible to compute a percentage error difference.

Figure 5:
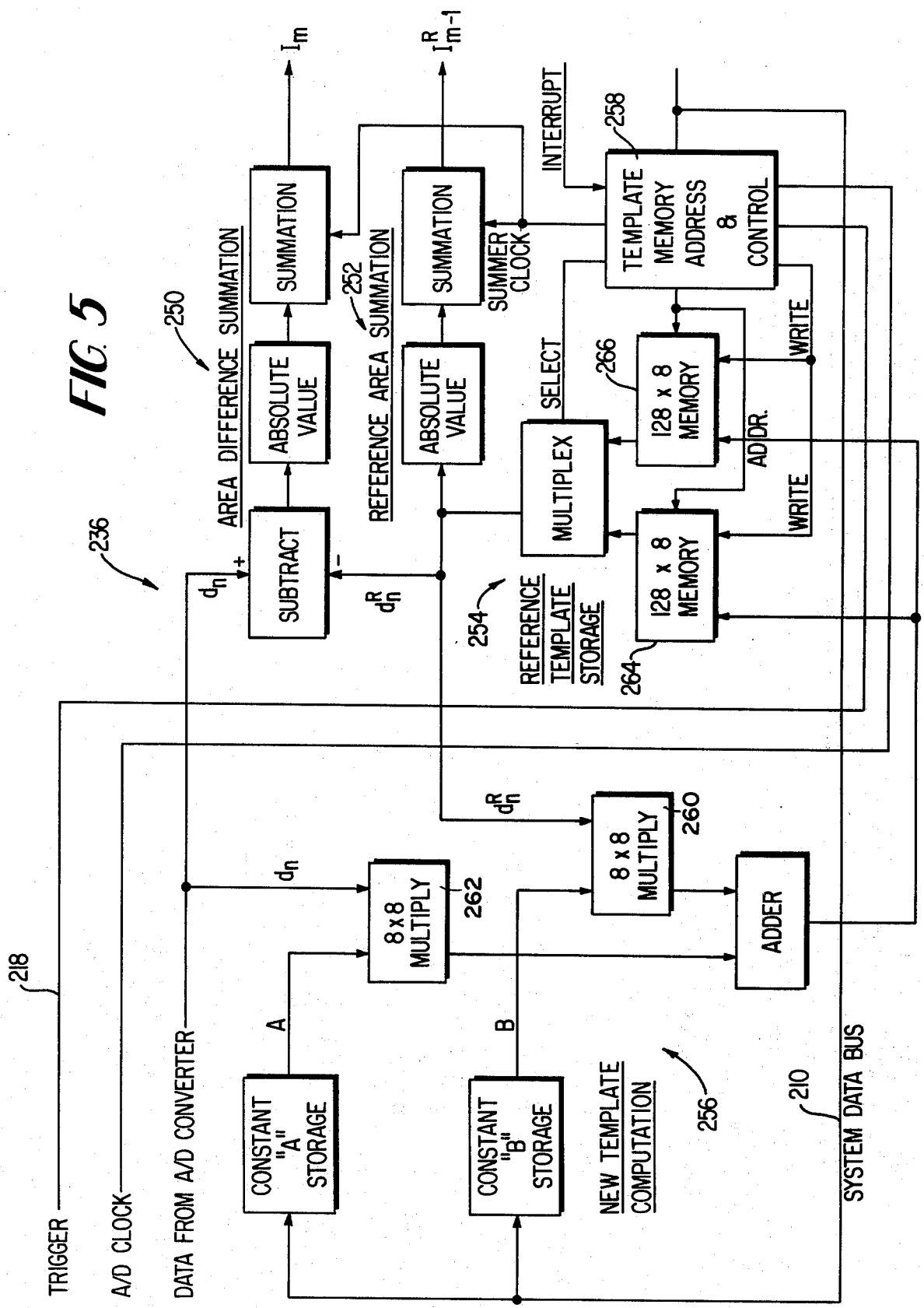
FIG. 5 is a block diagram of the area difference computation unit of the arrhythmia detection and scanning system 200 of FIG. 4.

FIG. 5 shows the area difference computation unit in more detail. The area difference unit 236 is divided into five major subsections: the area difference summation 250, the reference area summation 252, the reference template storage 254, the new template computation 256, and the template memory address control 258. For each QRS complex that is encountered, the area difference summation elements 250 will produce a 16-bit unsigned number, $I_m$, which represents the area of the shaded region in FIG. 2. The number $I_m$ is based on the following equation:

$$I_m = \sum_{n=0}^{N} |d_n - d_n^R|$$

where $d_n$ are sample points from incoming QRS complexes, and $d_n^R$ are corresponding sample points in the reference template. $I_{m-1}^R$ is computed by the reference area summation units 252. The area $I_{m-1}^R$ is given by the equation:

$$I_{m-1}^R = \sum_{n=0}^{N} |d_n^R|$$

The stored reference template is continuously updated as the electrocardiogram tape is analyzed and the new reference template is computed as a weighted average of the sample points from the incoming QRS complex and the old reference template. Sample points in the new reference are found by the following equation:

$$(d_n^R) = Ax(d_n)_m + Bx(d_n^R)_{m-1}$$
$$(n = 1, 2, 3 \ldots N)$$

where $(d_n^R)_m$ are samples in the new references, $(d_n)_m$ are the samples from the incoming QRS complex, $D_n^R(m-L)$ are the samples in the old reference, and A and B are constants.

The constants A and B are fractions which lie between 0 and 1 and are set by the microprocessor 212 of FIG. 4. Nevertheless, typically, A and B are selected such that $A=1-B$. Accordingly, the new template computation represents a discrete time low-pass filter which can track slow changes in the QRS complexes. This portion of the area computation unit 256 is made up to two 8-bit by 8-bit multipliers 260 and 262. The reference template storage section 256 employs two digital memories 264 and 266 which permit a new template to be generated without destroying the old one. One block of this memory retains the old template while the new template is written into the other block of memory. When the control section 258 receives an update template command from the microprocessor 212 of FIG. 4, the role of the two memory blocks is exchanged so that the newly generated template is retained as the reference template while the new one is written in.

The template memory address and control unit 258 produces control signals which drive the other portions of the area computation unit 236. This unit 258 contains programmable registers, which control the number of sample points used in the area difference computation. This is the number N appearing in the previous equation. The area difference computation is initiated by trigger pulses from the beat detector 216 and the control section produces an interrupt request which is placed onto the arrhythmia processor system bus 210 and is then provided to the template memory address and control unit 258. This interrupt signal informs the microprocessor 212 that a beat has been encountered and the microprocessor 212 then reads the data placed onto the system bus 210 by the various units on the left-hand side of the system bus.

More specifically, the various registers in the system shown in FIG. 4, which contain data extracted from the electrocardiogram waveform, are connected to a bus interface circuit 210 which permits the microprocessor 212 to read the various registers as though they were memory locations. The microprocessor 212 can also write, to various registers, such information as the constants A and B, the number of points N, the time setting of the clock circuit 208, and the refractory period in the beat detector 216. After the microprocessor receives the interrupt from the system, it reads the data extracted from the electrocardiogram. By using the floating point process, the percent difference in area and the percent difference in the interval time can be computed. Based on these two parameters and the pulse width, the microprocessor classifies the beats as normal or as one of several different types of subclasses of abnormalities identified above.

Figure 6:
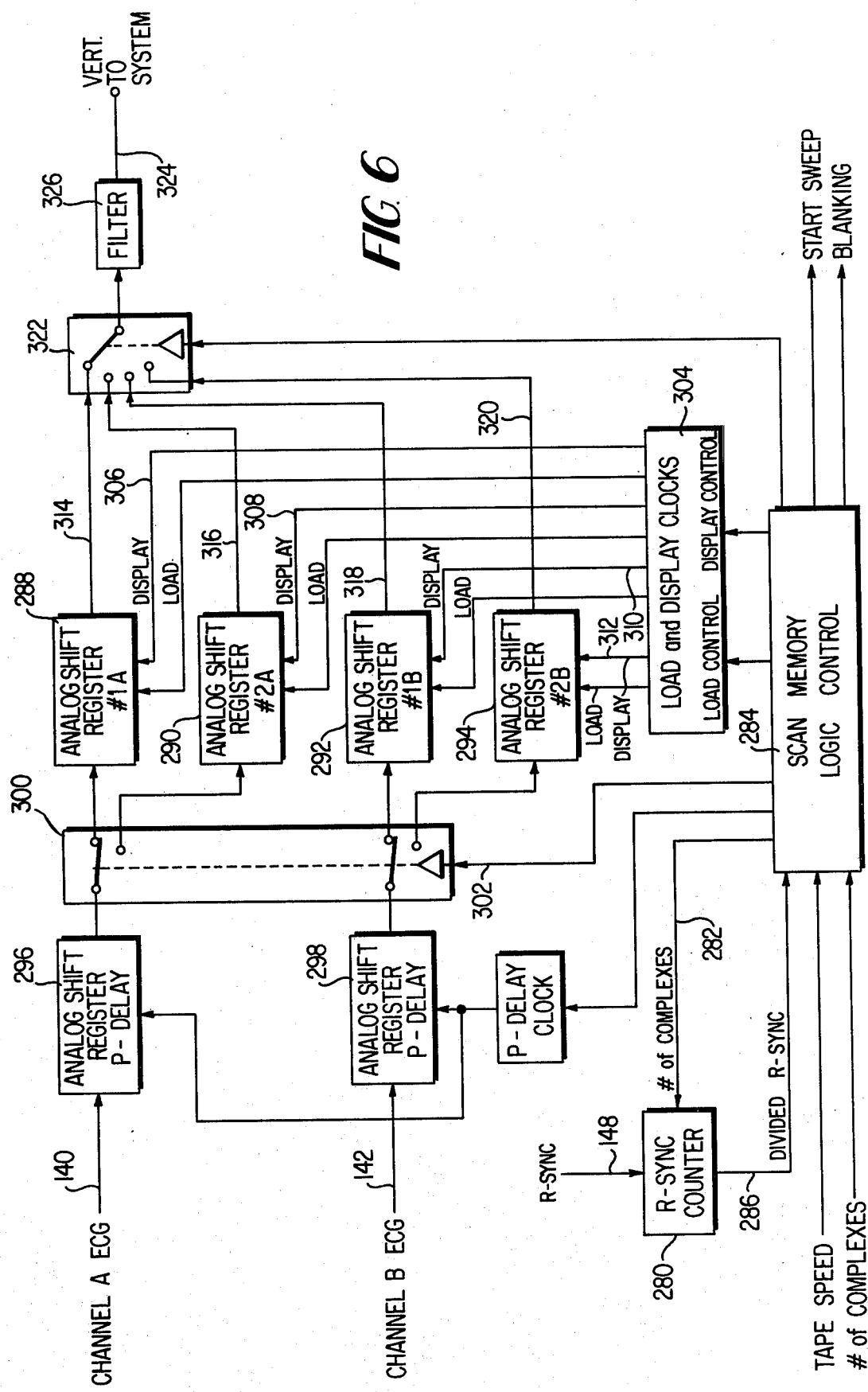
FIG. 6 is a block diagram of the scan memory 144 of FIG. 3.

Turning now to FIG. 6, the scan memory 144 is shown in more detail. In this figure, it may be seen that the electrocardiogram information on channel A is provided on line 140 and the electrocardiogram information on channel B is provided on line 142. Similarly, the R sync information is provided on line 149 to an R sync counter 280. The R sync pulses are produced upon detection of each QRS complex, as described above. These R sync pulses are provided to the R sync counter which is constructed to divide these pulses by the number of complexes which are intended to be displayed upon the screen. This number of complexes is provided to the R sync counter 280 on line 282 which stems from the scan memory control logic unit 284, which has, as its input, a signal from the front panel switches. In other words, the operator has selected the number of complexes which he wishes to have displayed on the screen. The output of the R sync counter 280 on line 286 is used to control the loading of analog shift registers which will receive the input data. These analog shift registers are sometimes termed bucket brigade devices and, in the present embodiment, four of these registers are employed, 288, 290, 292, and 294. Each of these units is a 1,024 bucket analog shift register.

Because the nature of the electrocardiogram signal is such that the QRS portion of the complex is distinct, it is only natural that this QRS wave be used to trigger the entire system. However, very important diagnostic information exists before the QRS portion of the complex and, accordingly, triggering from the QRS complex would lose a good portion of this important data. Therefore, the present invention provides a circuit wherein the data in each channel is displaced by a controllable amount of time by employing a pair of analog shift registers 296 and 298. These registers may be thought of as the "P" wave delay registers. The function of these two "P" wave delay shift registers is to offset the beginning of the electrocardiogram data to coincide with the R sync pulse. This time delayed or time shifted electrocardiogram data is then alternately loaded into a respective pair of analog shift registers, i.e., for channel A it is registers 288 and 290, and for channel B it is registers 292 and 294. The electrocardiogram data is loaded into the first analog shift register 288 until the output pulse of the R sync counter 280, which is fed to the scan memory logic control 284, causes the analog switch 300, via a signal appearing on line 302, to switch the input and direct the electrocardiogram data into the second analog shift register 290. Therefore, it may be seen that, while one of the pair of analog shift registers is being loaded with electrocardiogram data, the alternate shift register is available for shift out and display. A clock circuit 304 is provided to direct clock signals to the shift registers for shift out, and this unit 304 produces display signals on lines 306, 308, 310 and 312 which are inhibited for a selected period of time in order to permit the beam in the cathode ray tube display to retrace. After retrace, the analog shift register which is to be displayed is clocked by an appropriate signal on lines 306, 308, 310, 312, and the data stored in the appropriate shift register is dumped out on output lines 314, 316, 318 and 320 and provided to an analog switch 322. This data is dumped out of the analog shift registers at a rate which is much faster than the rate at which it was loaded and, accordingly, is displayed on the CRT at this higher rate. Prior to providing the signal on line 324 to the oscilloscope, a high frequency filter 326 is employed to eliminate any noise caused by the various switching taking place in this unit. Both of the channels operate in the identical manner with the exception that the analog shift register which has been loaded with the electrocardiogram data is not displayed until after the first channel has been displayed.

The ratio of shift-in speed to shift-out speed is such that there is much more than sufficient time to output both channels to the CRT before the next output of the R sync counter.

Two further items should be mentioned. First, referring to the tape speed control during automatic scan, the arrhythmia processor 212 (FIG. 4) stores raw data from the area difference unit 236 and R-R interval circuit 228 in a buffer (not shown), called FIFO (first in-first out), as each beat occurs. Beats which occurred earlier are classified using the data stored in the FIFO while waiting for the next beat to occur. If the current heart rate on the tape is so high that data is loaded in the FIFO faster than the data can be used, then the tape speed will automatically be lowered so that FIFO does not overflow. The automatically controlled tape speed permits efficient use of processing time because processor time is not wasted waiting for beats to occur when heart rate is low, as might happen if the tape speed were fixed so that the highest heart rate could be accommodated.

Second, the freeze memory controller 156 (see detailed discussion below) consists of conventional LSI microcircuits, including DMA counters such as the AMI 2940. Utilizing these circuits, the RAM is accessed directly via the DMA devices and the data is then read onto the bus to be displayed.

Figure 7:
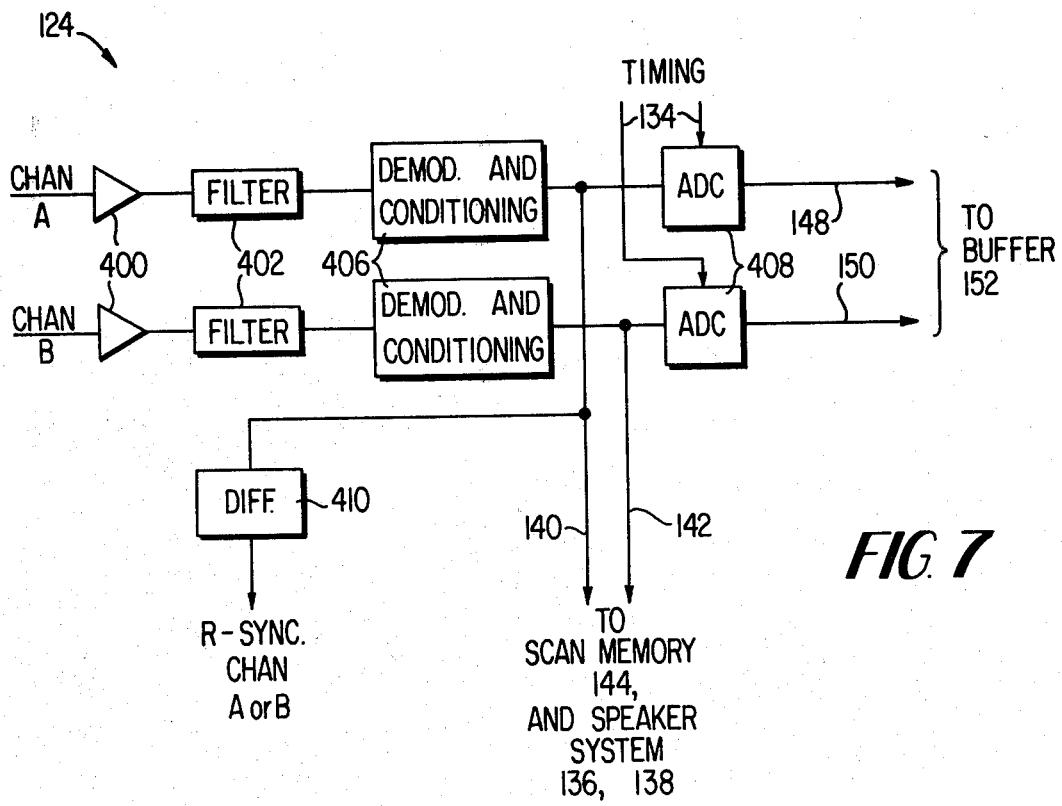
FIG. 7 is a block diagram of the converter 124 of FIG. 3.

FIG. 7 is a block diagram of the converter 124 of FIG. 3. As seen therein, the converter 124 of FIG. 3 comprises amplifiers 400 for amplifying the data inputs from channels A and B, respectively, filters 402 for filtering the received signals, and demodulating and conditioning circuits 406 for demodulating and conditioning the received signals. The signals obtained at this point are provided to the scan memory 144 and speaker system 136, 138 (FIG. 3). Moreover, one of the signals obtained at this point is provided to a differentiation circuit 410, by means of which RSYNC for channel A (or channel B, alternatively) is obtained. The latter is an important timing signal provided to the scan memory 144 of FIG. 3.

The converter 124 of FIG. 3 is further seen to comprise analog-to-digital converters (ADC) 408 which convert the demodulated and conditioned output signal to digital form, the digital data for channels A and B, respectively, being provided on output lines 148 and 150, respectively, to the buffer 152.

FIG. 8 is a block diagram of the speed control unit portion of the input interface 132. It should be first noted that the input interface unit 132 comprises conventional data routing circuitry or ports (PIA's) for routing data between the various connected elements 120, 124, 152, and 154 of FIG. 3.

However, the input interface unit 132 has been specially adapted in accordance with the present invention so as to contain a speed control unit portion shown in FIG. 8. As seen therein, the speed control unit includes a port (PIA) 420 for receiving DATA and ADDR information from the CPU 126 (FIG. 3), for generating in response thereto a control word comprising an upper count value or limit for the counter 422. Counter 422, which is reset by an INITIALIZE signal from the tape transport 120, counts to the upper count (N) value indicated by the port 420. The arrangement further includes a flip-flop 424, which is set (via its S input) by the INITIALIZE command. When the counter 422 reaches its upper limit (N), the flip-flop 424 is clocked so as to change state (to the reset state). Thus, the output waveform 426 is obtained. Output waveform 426 is characterized by a duty cycle B. Moreover, the waveform 426 has a pulse duration A dictated by the counter upper limit N, as controlled by the CPU 126 of FIG. 3 (as just explained). Accordingly, the CPU 126 is able to program the pulse duration, and thus the duty cycle (which is set to have a value dictated by the relationship A=24% B).

To summarize, the CPU 126 can adjust the pulse duration A so that an increase in the pulse duration will cause the tape transport 40 to go slower, whereas a decrease in A will cause the tape transport to go faster. This, of course, is due to the fact that the output waveform pulses 426 are provided to the tape transport 40 (for driving the tape deck at the desired (programmed) speed).

FIG. 9 is a block diagram of the freeze memory controller 156 of FIG. 3. As seen therein, the freeze memory controller 156 comprises a port (PIA) 430, DMA counters 432 and 434, a gate 436, a divide-by-N circuit 438, and oscillator 440.

In operation, the oscillator 440, via the divide-by-N circuit 438, clocks the DMA counters 432 and 434 so that the counters 432 and 434 count at a prescribed rate. The CPU 126 of FIG. 3 provides a data input, as well as data identification data, to the port 430. That is to say, port 430 receives various data, at various times, from the CPU 126, and, based on the data identification input also received from the CPU 126, the port 430 provides the data to the appropriate element of the system. Two such inputs from the CPU 126 are a destination count, which is provided by the port 430 to the DMA counters 432 and 434, and a control signal (NOT FREEZE), provided via inverter 442 as a clock enable input to the DMA counters 432 and 434, respectively, and also provided directly to a gate 436.

Accordingly, during the freeze mode of operation, inverter 412 enables counters 432 and 434 to count in accordance with the clock inputs from circuits 438 and 440, the counters 432 and 434 counting until the destination count is reached. DMA counters 432 and 434 provide the lower and upper 8 bits of address information provided on address lines to the freeze memories 160 and 162 of FIG. 3.

When the system is not in the freeze mode, that is, when the system is in the scan mode or in the "write to chart recorder" mode, the gate 436 is opened by the control signal NOT FREEZE, and address data from the CPU 126 is provided directly to the address lines for provision to the freeze memories 160 and 162.

Thus, freeze memory controller 156 provides freeze mode accessing of memories 160 and 162 through successive locations thereof based on the DMA counters 432 and 434. Moreover, the controller 156 also provides, in the scan or "write to chart recorder" modes, the ability to directly address the freeze memories 160 and 162 from the CPU 126.

Figure 10A:
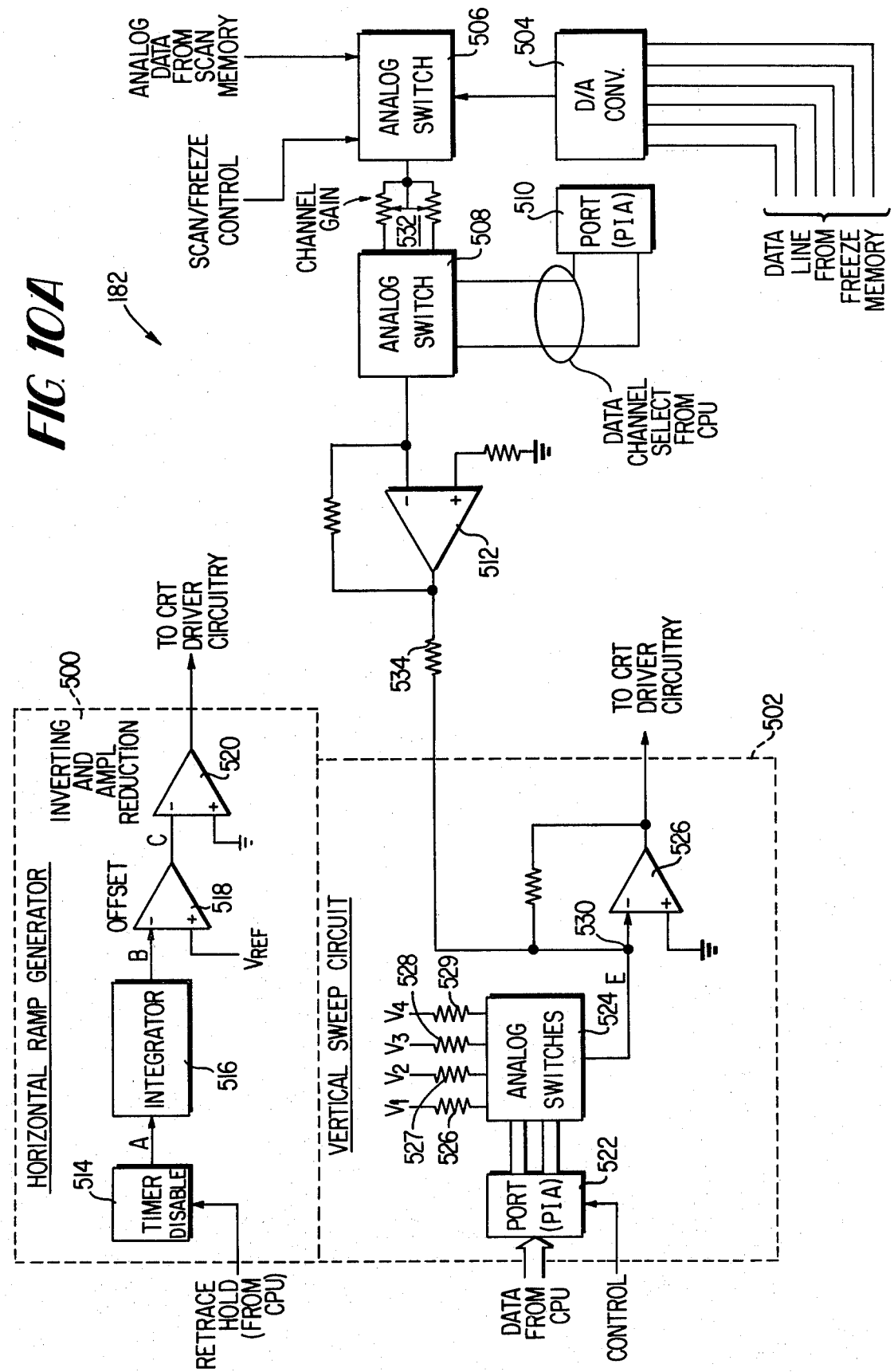
FIGS. 10A and 10B are, respectively, a block diagram of the CRT controller 182 of FIG. 3 and a timing diagram relating to the operation thereof.
Figure 10B:
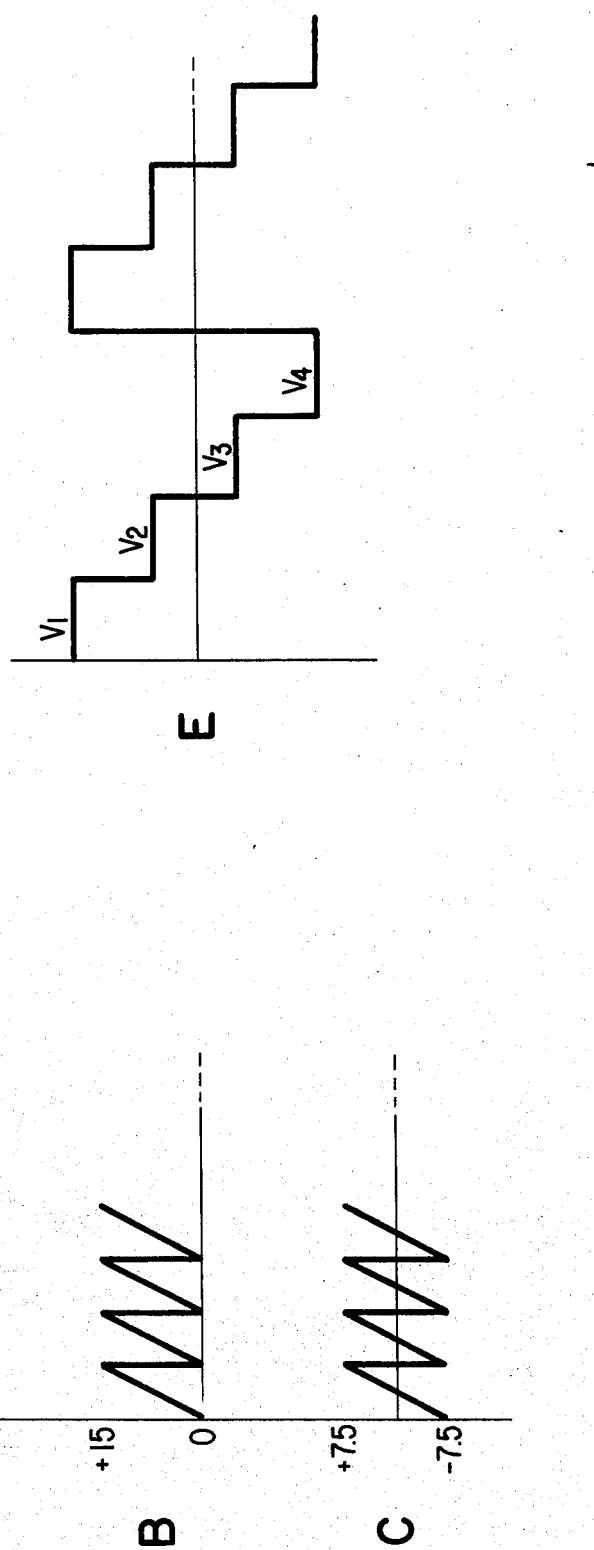

FIG. 10A is a block diagram of the CRT controller 182 of FIG. 3, while FIG. 10B is a timing diagram thereof. As seen in FIG. 10A, the CRT controller 182 comprises a horizontal ramp generator 500, vertical sweep circuit 502, digital-to-analog converter (DAC) 504, analog switches 506 and 508, port (PIA) 510, and amplifier 512.

In general operation, horizontal ramp generator 500 provides horizontal driving signals to the CRT driver circuitry (located in the conventional CRT scope 26 of FIG. 3). More specifically, horizontal ramp generator 500 comprises a timer 514, integrator 516, offset amplifier 518, and inverting amplifier 520. Referring to FIGS. 10A and 10B, the timer 514 issues negative going pulses A, which are provided to the integrator 516, the latter generating an output B representing a sawtooth wave. Offset amplifier 518 then adjusts output B (which ranges from 0 to +15 volts, in the preferred embodiment) so that output C ranges from −7.5 volts to +7.5 volts. Output C is then inverted and amplitude-adjusted in the amplifier 520, providing horizontal driver signals to the CRT driver circuitry.

Vertical sweep circuitry 502 is seen to comprise port (PIA) 522 for receiving data from the CPU 126 of FIG. 3 (the data, as previously explained, being identified by a control or identification input from the CPU 126, and thus routed to the appropriate element of the system). In this case, the port 522 routes the control data from the CPU 126 to analog switches 524. Analog switches 524 have associated inputs of variable voltage V1 through V4 (provided via resistors 526 through 529). In response to the input from the port 522, analog switches 524 select one of the variable voltages V1 through V4 for input to the negative input of the amplifier 526, the positive input of which is grounded. As a result, amplifier 526 issues a step voltage output E (see diagram of FIG. 10B), which constitutes the vertical driving signal of the CRT driver circuitry of the CRT 26 of FIG. 3.

It is to be noted that the input to the negative terminal of amplifier 526 includes a summing junction 530, which receives an output from amplifier 512. More specifically, analog switch 506 receives a scan/freeze control signal from the CPU 126, which designates which of the two modes (scan or freeze) is being implemented by the system. In response thereto, analog switch 506 provides either analog data from the scan memory 144 of FIG. 3 (in the scan mode) or data from the freeze memories 160 and/or 162 (in the freeze mode) to a further analog switch 508. In the latter case, the data from freeze memories 160 and/or 162 is provided as an analog input as a result of the operation of DAC 504.

Analog switch 508 has, at its input, a parallel potentiometer arrangement 532, by means of which channel gain for channels A and/or B is adjusted. The gain-adjusted analog signal is provided by analog switch 508 to amplifier 512 as a result of the reception of a data channel select signal from the CPU 126 via port (PIA) 510. The scan or freeze data is then amplified by amplifier 512 and provided via resistor 534 to the summing junction 530. In this manner, the scan or freeze data is superimposed on the vertical step waveform E. Thus, the single-beam CRT 26 of FIG. 3 can be employed, in accordance with the present invention, to display, in four separate lines on the CRT scope 26, the scan or freeze data provided to the summing junction 530.

FIGS. 11A–11G are flowcharts of various operations performed by the CPU 126 of FIG. 3. In general terms, the CPU 126 of FIG. 3 is a control processor which, under program control (as indicated by the flowchart of FIGS. 11A–11F), performs, among other things, the following functions: (1) interrogation of the front panel switches and buttons 154 of FIG. 3 to determine what operations are indicated by the operator's input thereto; (2) the issuance of various control signals to the front panel lamps and indicators 185 of FIG. 3 so as to light indicators corresponding to the various front panel switches and buttons depressed or various modes of operation of the system; (3) the issuance of control signals via the output card 184 of FIG. 3 (which is a conventional port (PIA), augmented by DAC circuitry (as is known to one of ordinary skill in the art)) to the chart recorder 14 so as to service the chart recorder in a manner which would be obvious to one of ordinary skill in the art, once he has chosen a particular chart recorder for implementation (that is, performance of the functions of interrogating memory and providing output, in a conventional manner, to the chart recorder 14 in accordance with the specifications thereof); (4) maintenance of a patient clock by means of deriving clock signals conventionally provided on the tape serviced by the tape transport 40 of FIG. 3; (5) programming of the tape playing speed (by means of the DATA inputs to the port 420 of FIG. 8, as previously explained with respect to the speed control unit portion of the input interface 132 of FIGS. 3 and 8); and (6) the provision of control inputs to the PIA's (that is, input interface 132, output card 184, among others, as previously described), thus achieving data routing through the PIA's.

Figures 11A, 11F:
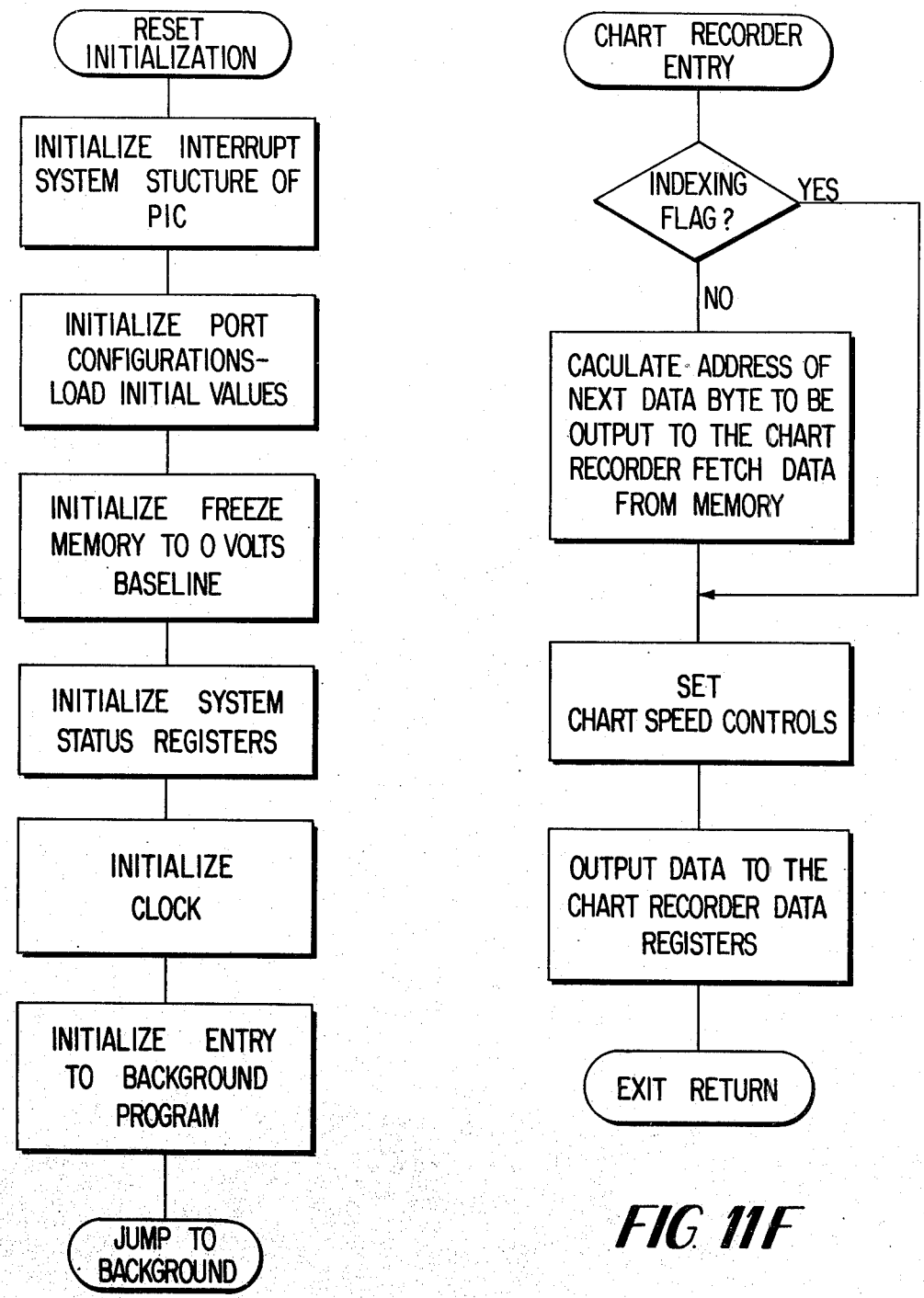
FIGS. 11A–11G are flowcharts of the operation of the CPU 126 of FIG. 3.
Figure 11B:
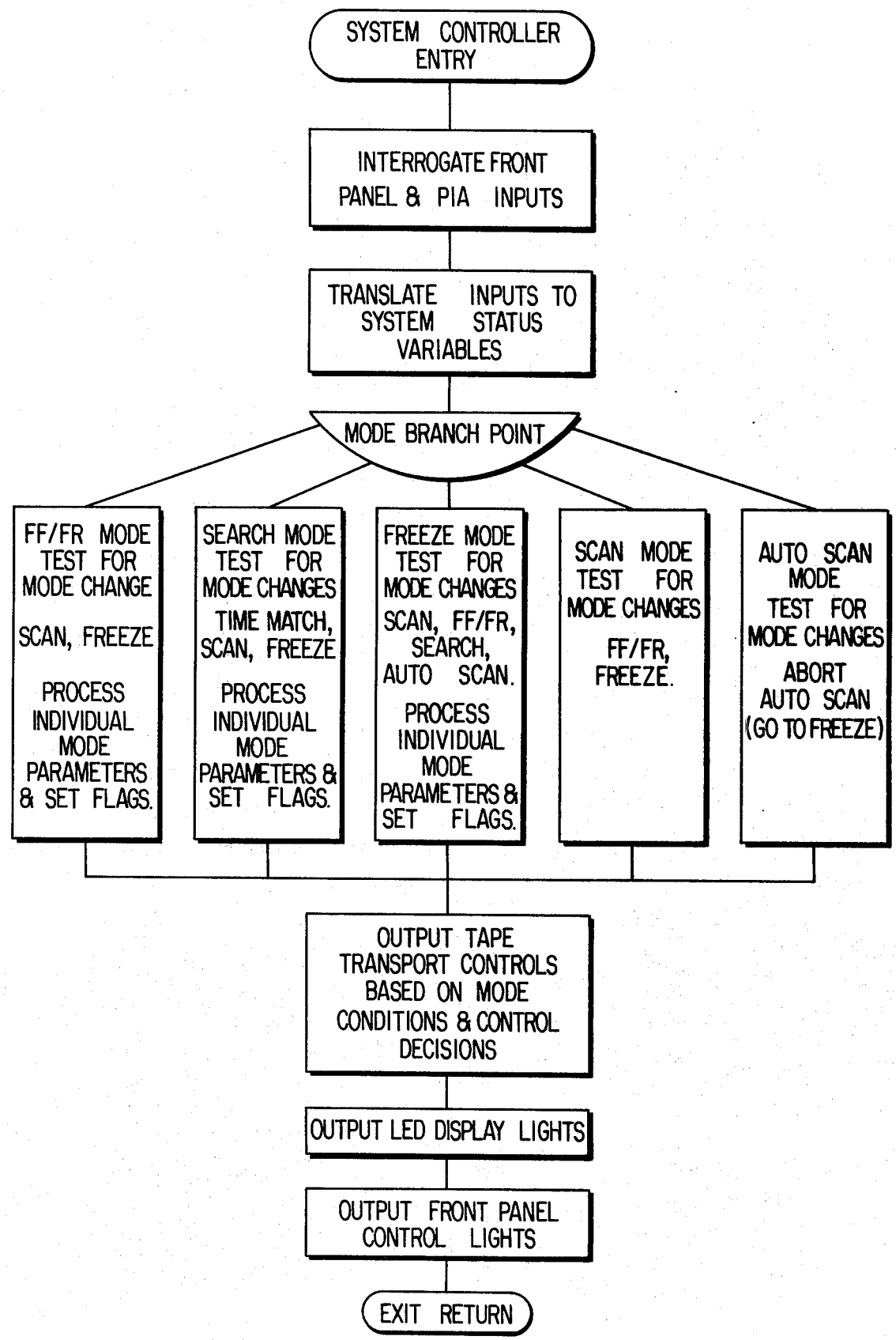
Figure 11C:
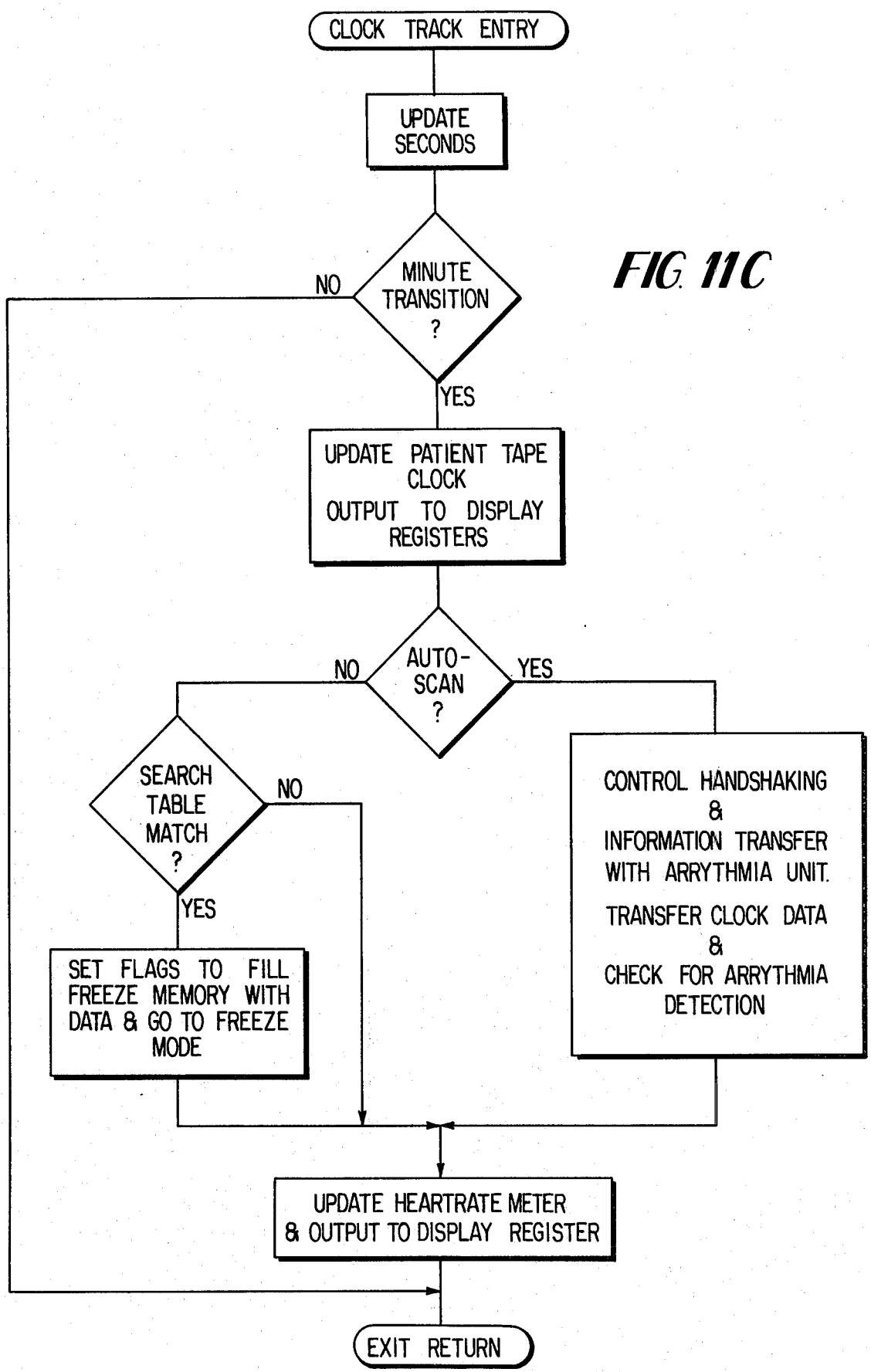
Figure 11D:
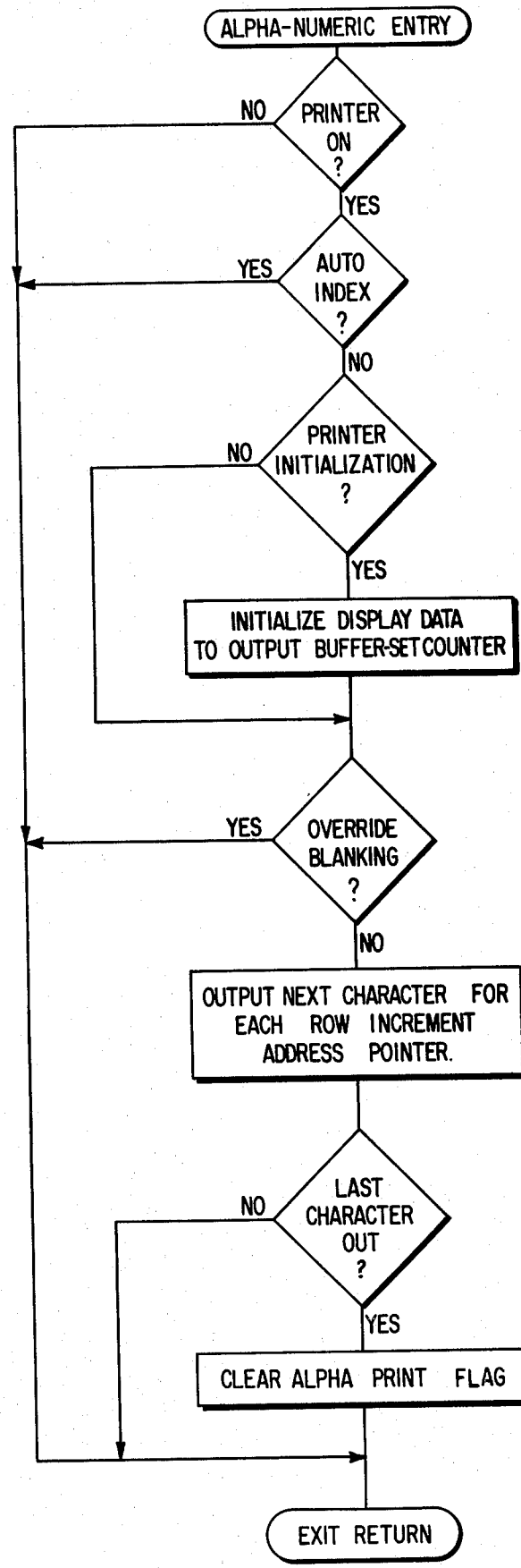
Figure 11E:
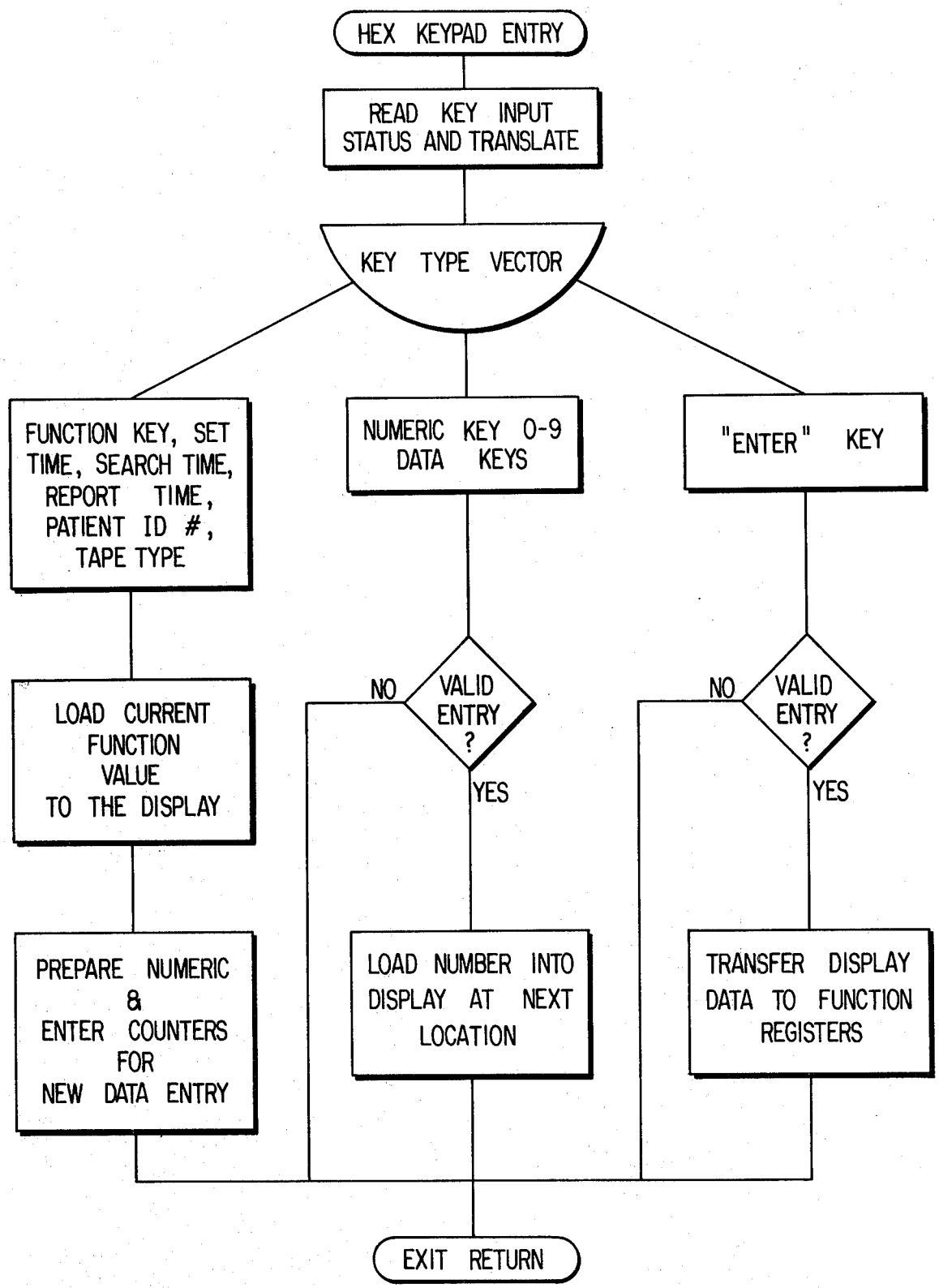
Figure 11G:
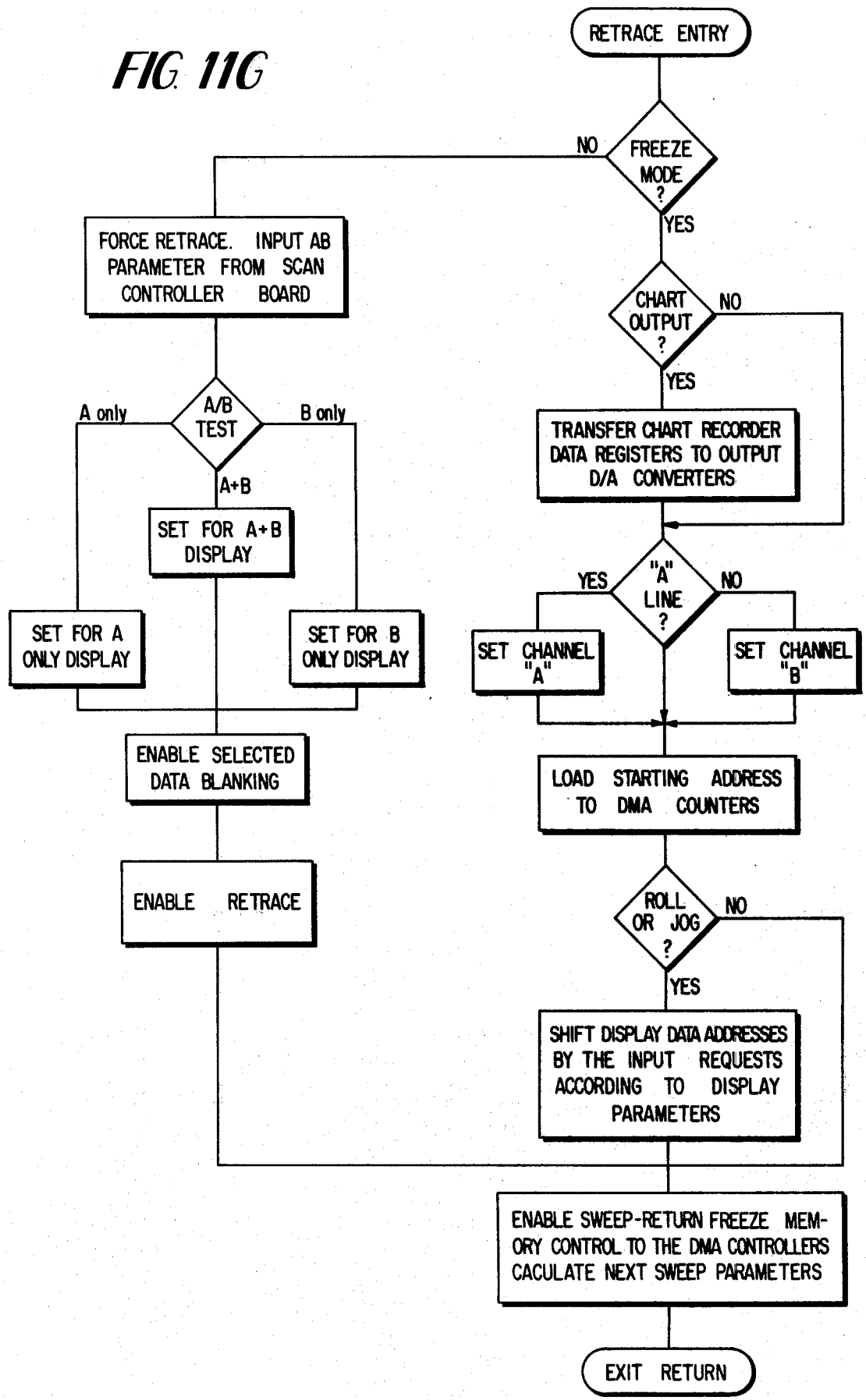

Thus, FIG. 11A represents a series of software operations for initializing the system; FIG. 11B represents a series of software operations for providing the main control functions (freeze mode, autoscan mode, fast forward, fast rearward, stop and freeze, etc.) implemented by the hardware of the system (as previously explained); FIG. 11C represents a series of software operations referred to as "CLOCK TRACK," by means of which the 60 Hz clock track from a Holter recording tape is read, as divided down to 1 Hz, the latter being used to maintain a patient clock; FIG. 11D represents software operations performed by the CPU 126 for the purpose of generating control signals for controlling the alphanumeric printer 133 of FIG. 3 (which is a conventional unit readily available on the market); FIG. 11E is a series of software operations, designated "hex key pad," performed in connection with provision of various displays, indications and outputs provided on the front panel lamps and indicators 185 of FIG. 3, as well as the various other display outputs (for example, 44 and 46) on the console 10 of FIG. 1; FIG. 11F is a flow chart of a "chart recorder entry" routine; and FIG. 11G represents a series of software operations performed in conjunction with the "retrace" operation of the conventional CRT 26 and the CRT controller 182.

It is to be understood that the above-described flowcharts of operations performed by the CPU 126 are merely representative of the perferred embodiment envisioned by the present inventors, and are therefore subject to modification so as to suit the particular display and functional needs of the system of the present invention, such modifications still falling within the scope of the claims appended to this application.

Figure 12A:
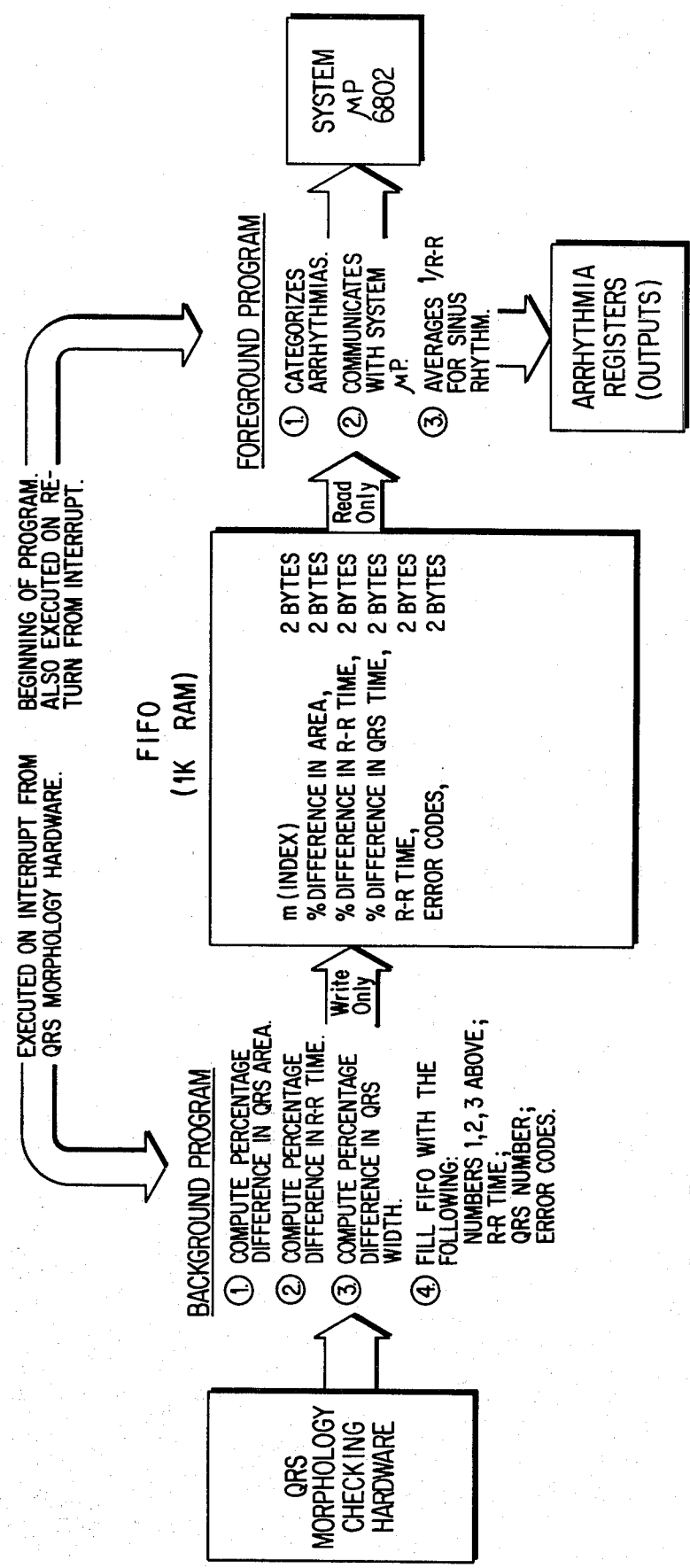
Figure 12B:
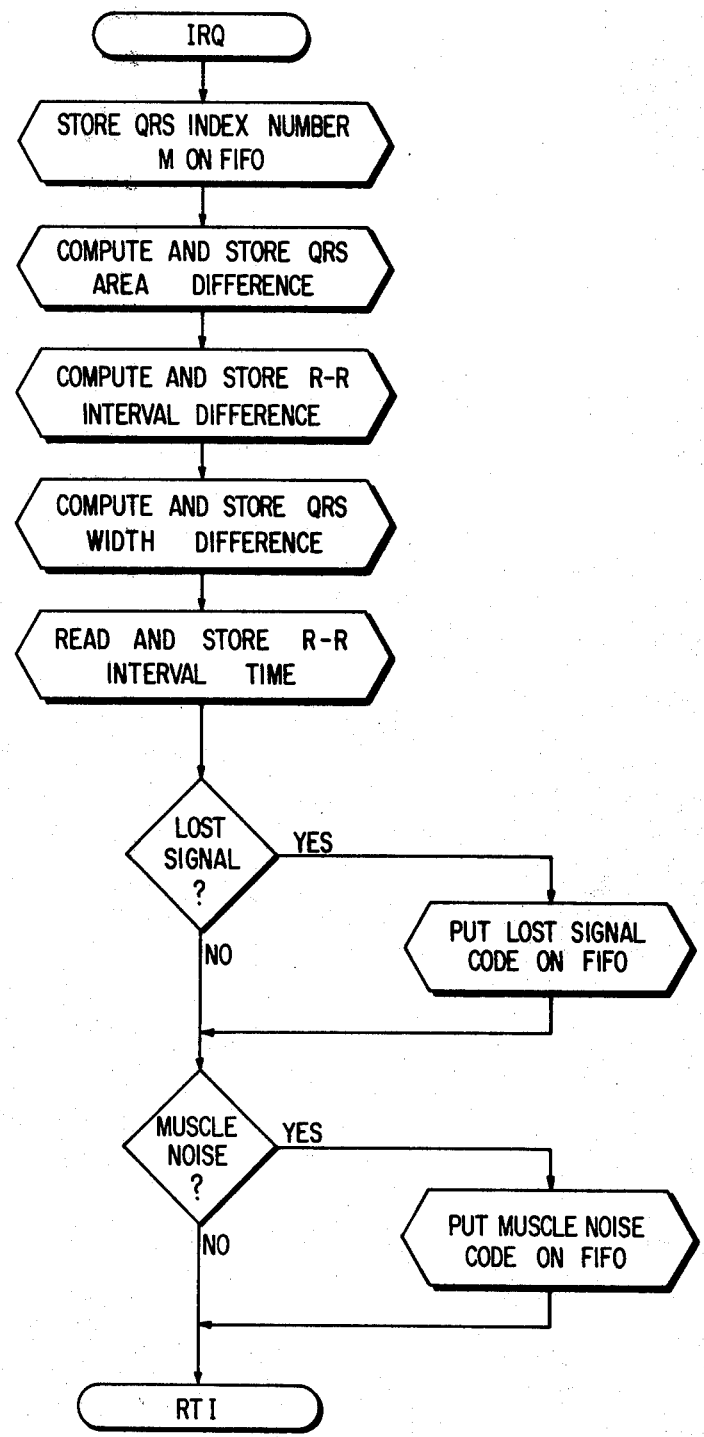
Figure 12C:
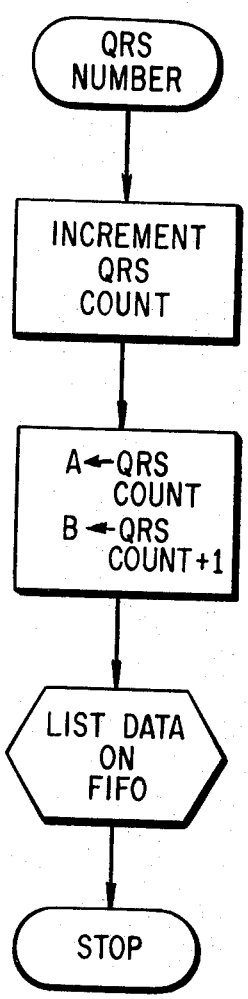
Figure 12H:
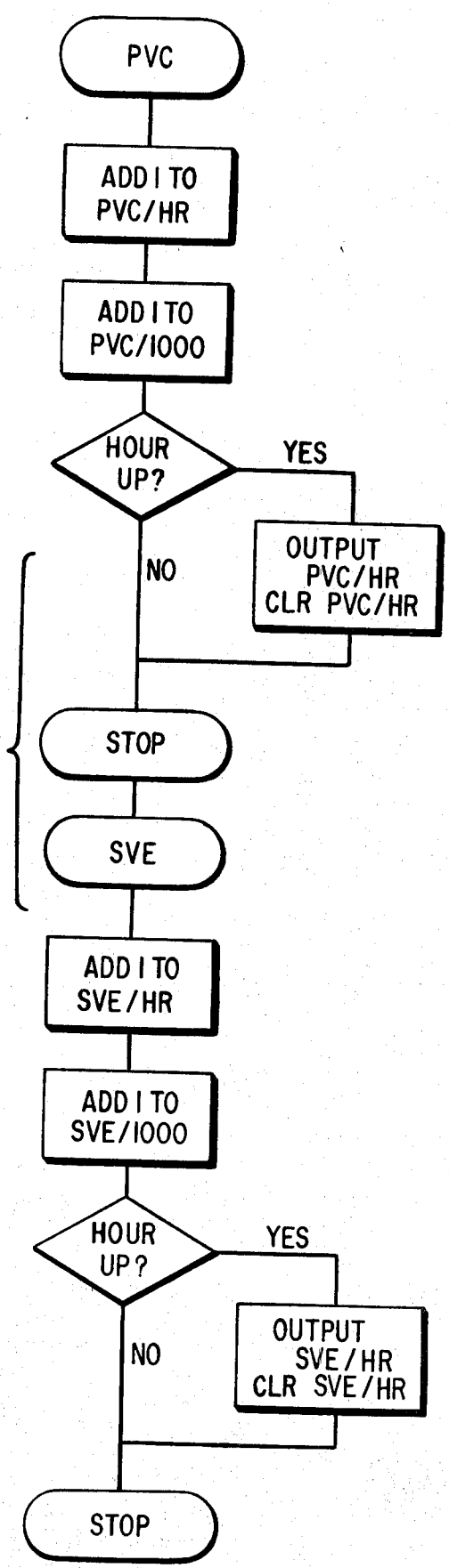
Figure 12D:
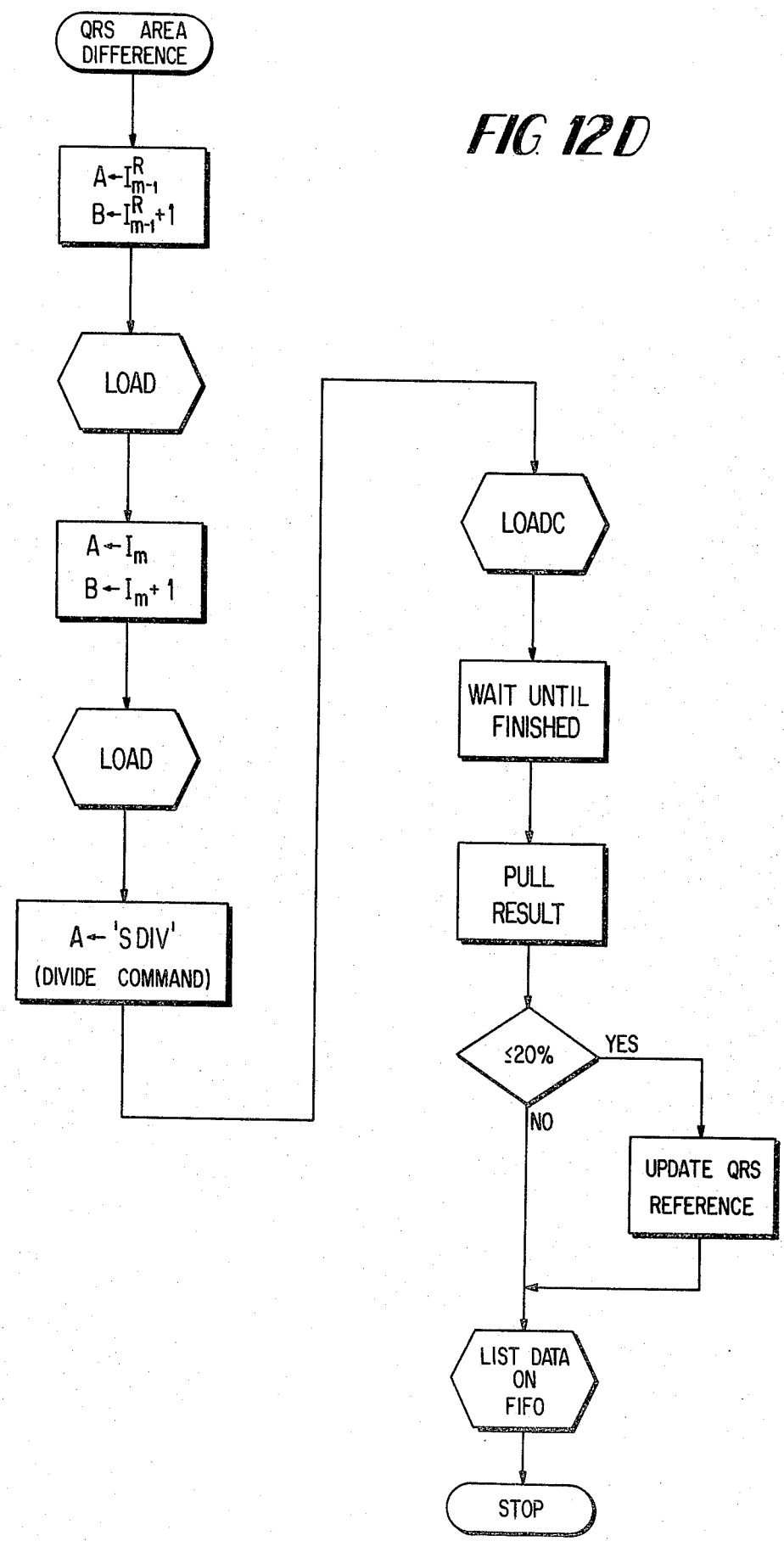
Figures 12E, 12F:
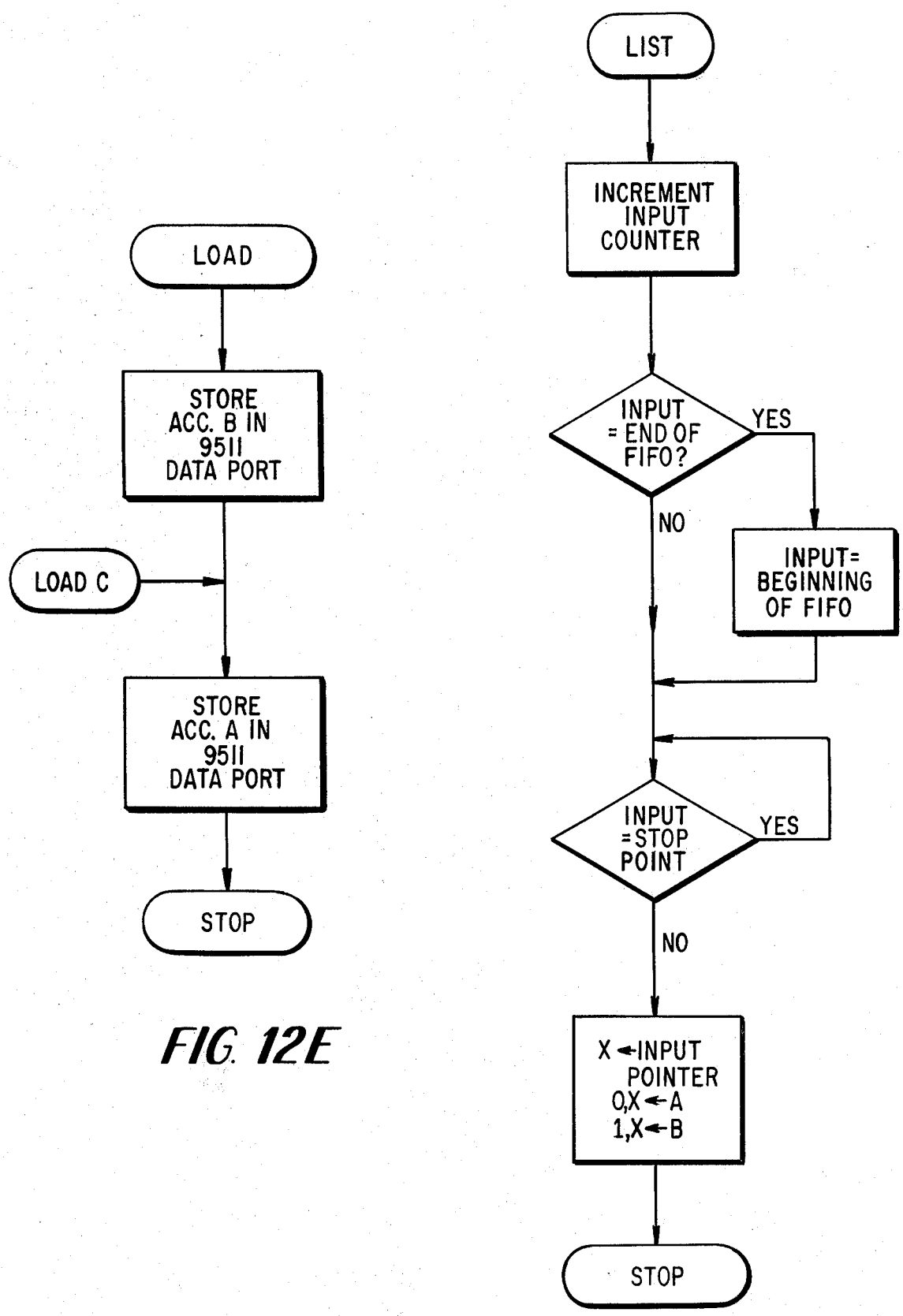
Figure 12J:
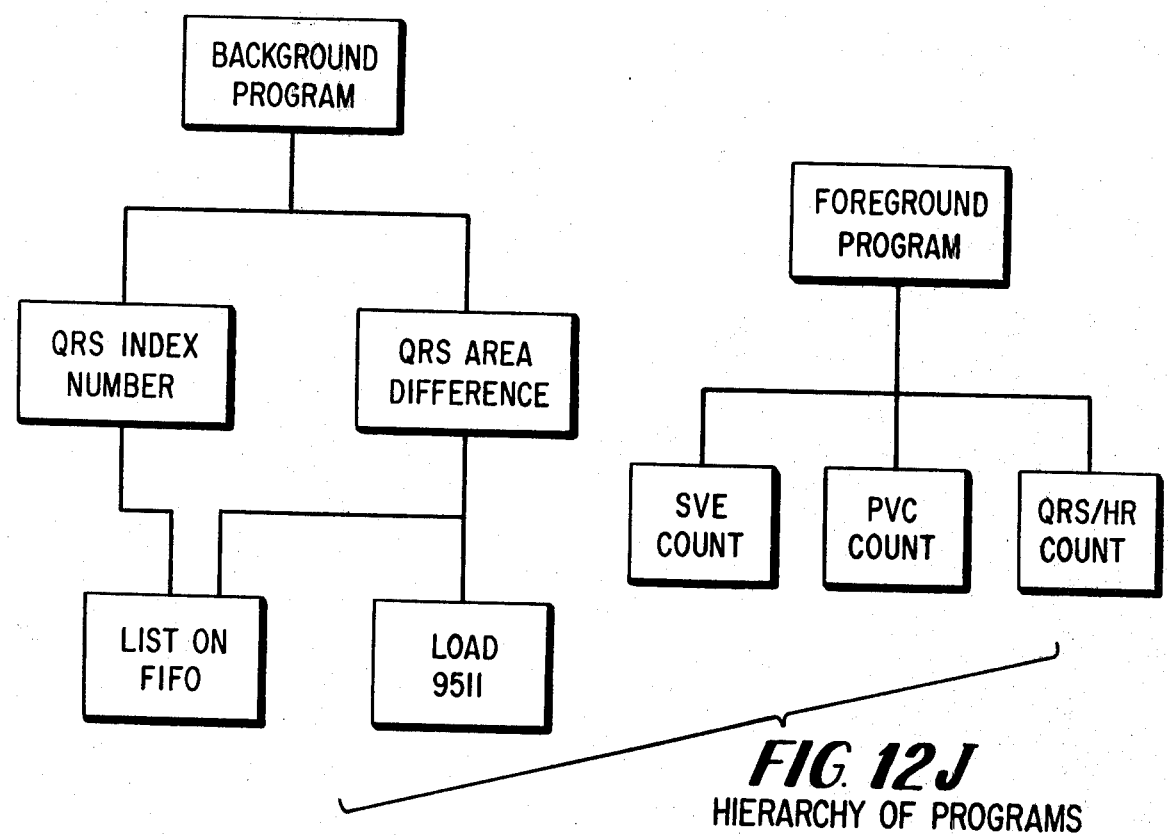
Figure 12I:
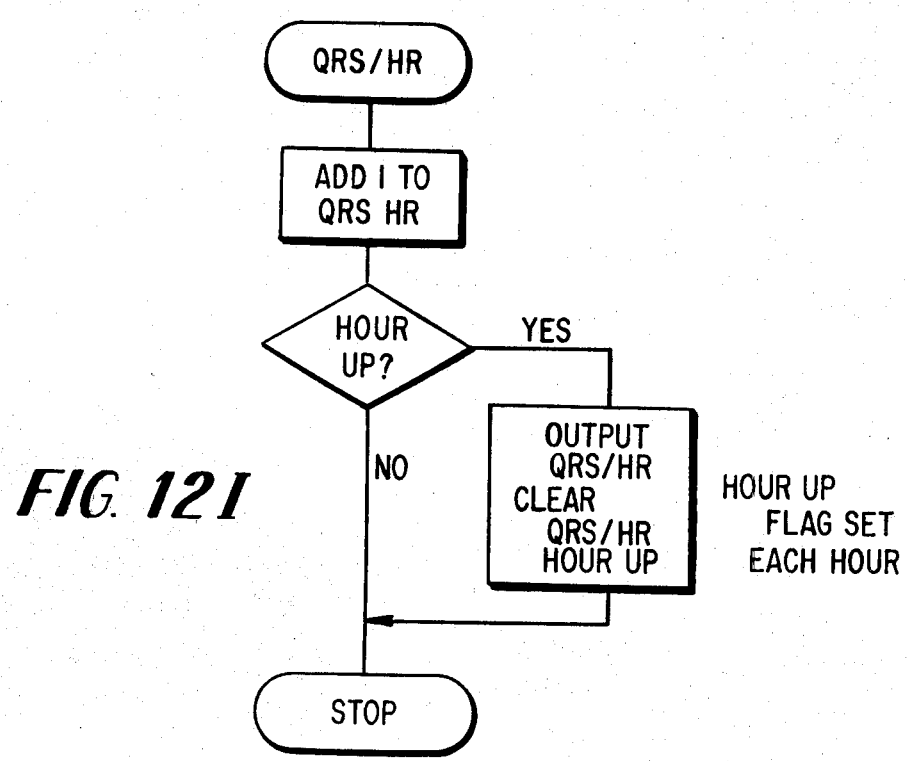

Finally, FIGS. 12A through 12J constitute a series of flowcharts of the operations performed by the microprocessor 212 of the arrhythmia detection and scanning system 200 of FIG. 4. More specifically, FIG. 12A is a general description of the background and foreground programs, respectively, performed by the microprocessor 212. FIG. 12B is a flowchart of an interrupt request (IRQ) routine performed by the background program implemented by the microprocessor 212. FIG. 12C is a routine performed by the microprocessor 212 with respect to the development of a QRS count for use by the arrhythmia detection and scanning system 200. FIG. 12D is a flowchart of the operations performed in conjunction with calculation of QRS area difference (per the aforementioned discussion of the "template" operation of FIG. 2). FIG. 12E is a flowchart of the "load" operation performed by the microprocessor 212. FIG. 12F is a flowchart of a data input control function performed by the microprocessor 212. FIG. 12G is a flowchart of the computational operations performed by the foreground program of the microprocessor 212. FIGS. 12H and 12I are flowcharts of various cumulative count operations (development of PVC per hour, SVE per hour, QRS per hour) performed by the microprocessor 212. FIG. 12J is a flowchart of the hierarchy of programs (background program, foreground program) implemented by the microprocessor 212, as described with respect to the previous flowcharts.

It is to be understood that the various flowcharts previously discussed contain operations which are obvious to one of ordinary skill in the programming art, upon a reading of the contents of the various detailed blocks, decision blocks, etc. of the various flowcharts. Thus, it is not necessary to discuss the various steps thereof in further detail, especially since such detailed operations would, as previously stated, be obvious to one of ordinary skill in the programming art, upon studying the aforementioned flowcharts as previously discussed.

It is understood, of course, that the foregoing is presented by way of example only, and is not intended to limit the scope of the present invention since various other embodiments and circuit arrangements are envisioned by the present invention. For example, the inventive system could be embodied to operate at speeds greater than 240 times the real time. Other modifications are also contemplated as being within the ability of one of ordinary skill in the art, and are understood to fall within the scope of the appended claims.

What is claimed is:

1. An adaptive cardiac diagnostic system for receiving electrocardiogram signals which have been prerecorded in dissimilar formats having different known parameters and for processing same in accordance with operator input, comprising:
   selector means responsive to said operator input for selecting one of said prerecorded electrocardiogram signals of dissimilar format;
   playback means for reproducing said selected one of said prerecorded electrocardiogram signals to develop reproduced signals;
   scanning and converting means for scanning and converting the reproduced signals to produce information signals;
   analyzing means for analyzing said information signals; and
   processor means for controlling said scanning and converting means and said analyzing means, said processor means being responsive to said operator input for variably controlling said scanning and converting means and said analyzing means in accordance with each dissimilar format based upon the different parameters of said format for said selected one of said prerecorded electrocardiogram signals.

2. An automatic arrhythmia processor for receiving and processing electrocardiogram (ECG) signals containing QRS complexes from a record, comprising:
   reference means for providing a reference QRS complex having an R-R interval and a reference area;
   comparing means responsive to said received ECG signals for comparing areas of successive said QRS complexes in said ECG signals to the reference area in said reference QRS complex to derive a difference area therebetween; and
   update means for continuously updating the R-R interval and area of the reference QRS complex in accordance with each comparison of the reference QRS complex to each successive said QRS complex.

3. The processor of claim 2, wherein said update means comprises a low pass filter which tracks changes in successive said QRS complexes.

4. The processor of claim 2, wherein said comparing means comprises an area difference summation circuit which computes a number representing the difference area between the area of said reference QRS complex and the area of said QRS complexes in said received ECG signals.

5. The processor of claim 2, wherein said reference means comprises a first portion for holding the reference QRS complex most recently updated, and a second portion for holding the reference QRS complex immediately preceding the reference QRS complex most recently updated.

6. An automatic, high speed, multi-mode scanning system for analyzing electrocardiogram data prerecorded on a tape, comprising:
   receiving means for receiving said electrocardiogram data so as to provide at least one channel of analog data as an analog output;
   scan memory means for scanning and storing said at least one channel of analog data;
   converting means for converting said at least one channel of analog data to corresponding digital data;
   freeze memory means for storing said corresponding digital data;
   control means for controlling read out of said corresponding digital data stored in said freeze memory means in a first mode of operation, and for controlling read out of said at least one channel of analog data stored in said scan memory means in a second mode of operation; and
   display means responsive to said output of said freeze memory means in said first mode of operation and to said output of said scan memory means in said second mode of operation for displaying said output of said freeze memory means in said first mode and said output of said scan memory means in said second mode.

7. The system of claim 6, comprising arrhythmia detection means for receiving and analyzing said at least one channel of analog data provided by said receiving means to detect arrhythmia included in said prerecorded electrocardiogram data.

8. The system of claim 7, wherein said electrocardiogram data includes QRS complexes having an area, and said arrhythmia detection means comprises an area difference computation unit for comparing the area of each successive one of said QRS complexes with an area of a reference QRS complex to derive corresponding difference areas representing the differences therebetween.

9. The system of claim 8, wherein said arrhythmia detection means further comprises a reference area unit holding reference data representing said reference QRS complex, and update means responsive to said comparison of said area of each successive one of said QRS complexes with said area of said reference QRS complex for updating said reference data.

10. The system of claim 9, wherein said reference area unit comprises a first portion for holding the reference data most recently updated and a second portion for holding the reference data immediately preceding the reference data most recently updated.

11. The system of claim 8, wherein said arrhythmia detection means further comprises a reference unit area for holding reference data representing said reference QRS complex, a beat detector for analyzing said electrocardiogram data to detect a beat corresponding to a peak of the QRS complex so as to develop a corresponding trigger signal, and update means responsive to said corresponding trigger signal for updating said reference data in said reference unit area.

12. The system of claim 7, wherein said freeze memory means includes successively accessible addresses, said system further including freeze memory control means for reading said corresponding digital data out of said freeze memory means, said freeze memory control means including means for receiving a control signal designating a designation count, and at least one counter for counting through successive count values, defining an output of said at least one counter, to said designation count, said output of said at least one counter being successively applied to said freeze memory means for accessing corresponding said successively accessible addresses thereof.

13. The system of claim 7, further including processor means for providing address data for selectively accessing said freeze memory means.

14. The system of claim 7, further comprising operator input means for selectively actuating said system to said first or second modes of operation, said display means including selecting means connected to said operator input means and responsive to selection of said first or second modes of operation for selecting data from said scan memory means or said freeze memory means, respectively, for display, said display means being connected to said selecting means so as to selectively display said data from said scan memory means or said freeze memory means, respectively.

* * * * *